United States Patent [19]
Wojciechowski et al.

[11] Patent Number: 5,873,990
[45] Date of Patent: Feb. 23, 1999

[54] HANDHELD ELECTROMONITOR DEVICE

[75] Inventors: Marek Wojciechowski; Frederick A. Ebeling, both of Cary; Robert W. Henkens; Najih A. Naser, both of Durham; John P. O'Daly, Carrboro; Steven E. Wegner, Chapel Hill, all of N.C.

[73] Assignee: Andcare, Inc., Durham, N.C.

[21] Appl. No.: 711,186

[22] Filed: Aug. 21, 1996

Related U.S. Application Data

[60] Provisional application No. 60/002,636, Aug. 22, 1995.

[51] Int. Cl.$^6$ .......................... G01N 27/26; G01N 27/28
[52] U.S. Cl. .......................................... 204/406; 324/450
[58] Field of Search .................................... 324/439, 445, 324/446, 450; 204/400, 406, 407, 403; 205/775, 779, 780, 789

[56] References Cited

U.S. PATENT DOCUMENTS

| | | | |
|---|---|---|---|
| 5,046,618 | 9/1991 | Baker et al. | 422/82.01 |
| 5,120,421 | 6/1992 | Glass et al. | 204/206 |
| 5,217,594 | 6/1993 | Henkens et al. | 204/403 |
| 5,366,609 | 11/1994 | White et al. | 204/403 |
| 5,437,772 | 8/1995 | Emory et al. | 204/153.1 |
| 5,468,366 | 11/1995 | Wegner et al. | 205/789.5 |
| 5,589,045 | 12/1996 | Hyodo | 204/406 |

FOREIGN PATENT DOCUMENTS

| | | |
|---|---|---|
| 0351516A2 | 1/1990 | European Pat. Off. |
| 0653629A2 | 5/1995 | European Pat. Off. |

OTHER PUBLICATIONS

International Search Report dated Feb. 3, 1997.
Naser et al., "Quantitative Testing for Lead in Environmental Samples using a Gold–Modified, Disposable Sensor and a Portable Monitor," *35th Annual Eastern Analytical Symposium & Exposition*, Abstract No. 411, p. 110, Nov. 17–22, 1996.
Wojciechowski et al. "Inexpensive, Easy to use and Portable Electrochemical Monitor and Disposable Sensors for Teaching, Research or Testing," *Book of Abstracts*, Pittcon '97, Mar. 16–21, 1997, Abstract No. 590P.
Naser et al. "Disposable Colloidal Gold Sensors for Environmental Diagnosis," *Book of Abstracts*, Pittcon '97, Mar. 16–21, 1997, Abstract No. 617P.
Zhang et al. "A Fast and Portable Electrochemical Immunosensor System," *Book of Abstracts*, Pittcon '97, Mar. 16–21, 1997, Abstract No. 618P.
Naser et al. "Development of a DNA Hybridization Biosensor for *E. coli* using Electrochemical Detection," *Book of Abstracts*, Pittcon '97, Mar. 16–21, 1997, Abstract No. 1246.
Wojciechowski et al. "Mediatorless, Disposable Hydrogen Peroxide Sensor Based on Colloidal Gold and HRP," *Book of Abstracts*, Pittcon '97, Mar. 16–21, 1997, Abstract No. 1249.
Wojciechowski et al. "Electroanalytical Applications of Disposable, Colloidal Gold Based Microarray Sensors," *Abstracts of Papers, Part 1*, 212th ACS National Meeting, Aug. 25–29, 1996, Abstract No. 003.
Wojciechowski et al. "A Fast and Simple Method for Direct Determination of Lead in Whole Blood Using Cholloidal Gold Modified Disposable Sensors and a Single–Key Electrochemical Monitor," *The Pittsburgh Conference Presents Pittcom '96*, Chicago, Mar. 3–8, 1996, Abstract No. 1037.

*Primary Examiner*—Robert Warden
*Assistant Examiner*—Alex Noguerola
*Attorney, Agent, or Firm*—Arnold, White & Durkee

[57] ABSTRACT

An apparatus is disclosed which is a microprocessor based instrument designed to conveniently and rapidly measure various analytes in environmental and biological samples. The instrument operates as a stand-alone unit powered by a battery or a DC power module and may be equipped with a communication port allowing uploading test results to a computer. Several unique electronic, microchip and software configurations were developed for the device to make it a portable, low-cost, safe, automated and simple-to-operate instrument particularly adapted for precise and accurate measurement of metal ions such as heavy metals such as lead in human blood.

5 Claims, 22 Drawing Sheets

· # HANDHELD ELECTROMONITOR DEVICE

BACKGROUND OF THE INVENTION

This application claims the benefit of U.S. Provisional Application No. 60/002,636 filed Aug. 22, 1995.

A portion of this patent document contains material which is subject to copyright protection. The copyright owner has no objection to the facsimile reproduction by any one of the patent disclosure, as it appears in the Patent and Trademark Office patent files or records, but otherwise reserves all rights whatsoever.

A copy of the computer program listing is provided as an appendix in the patent file which will not be printed, but will be available subsequent to the grant of patent or when the application is otherwise made publicly available.

FIELD OF THE INVENTION

The invention relates generally to a convenient microprocessor based instrument adapted to measure low levels of analytes in fluids. More particularly, the disclosed devices are automated, portable electrochemical instruments designed to accept various chemically modified electrode sensors and to rapidly and accurately measure low levels of various analytes. Hand-held electromonitors are described that are capable of employing various electrochemical analytical techniques for the precise and accurate measurement of multiple analytes in a wide range of fluids.

DESCRIPTION OF THE RELATED ART

Recently, the development of highly efficient electrochemical stripping sensors based on colloidal gold has resulted in the development of rapid, simple tests for determining trace amounts of contaminants, particularly heavy metals and especially undesirable environmental toxins such as lead and mercury. The sensors for detection of these metals are basically colloidal gold modified electrodes where the surface appears to act as a microelectrode array, possibly providing a rationale for the superiority of these electrodes over bulk gold electrodes. The preparation of colloidal gold electrodes is described in several patents, including U.S. Pat. Nos. 5,334,296; 5,391,272; 5,217,594; and 5,368,707 all of which are incorporated herein by reference and in their entirety.

Colloidal gold based electrodes have been used not only for potentiometric measurement of analytes, but also in square wave coulometric determination of metal ion levels. Square wave coulometry (SWC) combines fast scanning square wave voltammetry with coulometric measurement of the signal and has been used in some applications as preferable to differential pulse voltammetry. The advantages of this method with respect to sensitivity and speed over other voltammetric techniques is discussed in detail in U.S. Pat. No. 5,468,366, the entire disclosure of which is herein incorporated by reference. The reference particularly mentions that one advantage of SWC analysis for measurements involving microelectrode arrays is that it does not require removal of dissolved oxygen from the sample solution in contrast to other stripping techniques.

SUMMARY OF THE INVENTION

In a general aspect the invention employs combinations of electrodes in an electrolyte to generate electrical signals which are indicative of the concentration of an analyte in the electrolyte. The signals are digitized and processed in digital form to determine and display the signals. The electrodes in contact with a sample of the electrolyte are contained in a small fixture or probe which is electrically coupled to a data processing system. This system is housed in a container or housing which is small enough to be hand-held.

The invention also employs special means for calibrating the instrumentation. One such means makes use of calibration strips which are coupled to the data processing system in a manner similar to the electrodes. Calibration data from a calibration strip may be transferred into the system or it may indicate to the system which set of calibration data to employ from sets which are already stored in the system as in a "lookup" table. In general, a particular calibration strip is provided for a given set of electrodes, or for a given lot of such electrodes.

An alternate calibration system may employ a microchip on which calibration data for a given set of electrodes has been stored. A microchip reader on the instrument reads and transfers the calibration data from the microchip into the data processing system.

In general, the invention measures a parameter of the electrode signal, notably the currrent, for the analysis made by the invention. Thus, the system may measure amperage, or a modulated amperage signal to perform analyses based on amperometry, voltammetry, square wave coulometry, etc. Anodic stripping voltammetry is particularly preferred in analyzing for metals in one typical application.

The advent of the colloidal gold electrodes marks a great step forward in the analysis of metals and contaminants. The present invention marks a further advance in recognizing the need for an instrument for making such analyses which is readily portable but also accurate and flexible. Especially attractive is an instrument which is self-contained and sufficiently compact to be hand held. Such an instrument is particularly advantageous in remote operations and provides results which are not only accurate but also prompt and cost-saving. It is apparent that such an instrument may be used in the laboratory as well as in the field.

The present invention provides an instrument which combines unique electronic, microchip and software configurations in a device that is portable, safe, automated and simple to operate in determining analyte concentrations in fluid samples. In particular aspects, an apparatus for analyzing for a selected analyte in blood, urine or water is provided. Such a device is small enough to be hand held and can be set to determine virtually any metal ion, in addition to peroxides, glucose, proteins, drugs and pesticides. The disclosed device may be conveniently set up for use with various electrochemical analytical techniques such as square wave coulometry, anodic stripping voltammetry, and amperometry, thereby providing several advantages over other conventional electrochemical instruments.

The disclosed microprocessor-based device is designed to perform various tasks associated with the measurement of electrochemical sensor response. The sensor is used as a disposable insert with this monitor. In one embodiment, designated the LeadCare™ Monitor (AndCare, Inc., Durham, N.C.) for specifically measuring blood lead levels, the instrument has one mode of operation which is a blood lead level (BLL) measurement initiated by pressing a pushbutton switch ("START"), after insertion of the sensor into the monitor and placing a sample on the sensor. In less than 2 minutes a BLL will be displayed on the LCD.

The monitor incorporates several distinctive functions and features, some of which are new in this type of device, that include:

Single Push-Button Operation

This is an improvement over portable electrochemical devices available on the market, none of which is for blood lead. They all require at least a few step long set up/initiation procedures.

Sensor Recognition Test

A novel feature of the device is that it is set up to run a test to distinguish whether a calibration strip or a test sensor is connected when the test sequence is triggered by the START button.

The test is based on the difference in the current vs. time characteristics of a calibration strip and a test sensor. When a voltage pulse is applied a constant (i.e., time independent) current is generated by resistors of the calibration strip. The test sensor containing sample solution on the other hand produces current that sharply decays in time.

The device applies a small voltage pulse to the connector and current is sampled several times over a few millisecond period. If a constant (±10%) current is detected, the system assumes that a calibration strip is connected and the software initiates resistance measurement of the calibration strip. If a decaying current is detected, the software goes to the BLL measurement cycle.

Automatic Calibration

An additional novel feature of the device is the sensor calibration scheme which eliminates complicated and time consuming manual calibration procedures required by currently available devices. The scheme involves a resistor network-based calibration strip and sensor calibration database stored in the EEPROM. It does not require operator intervention except insertion of the calibration strip and pressing the START button. The system first recognizes that a calibration strip is connected and measures the resistance of two resistors on the strip. Based on the values obtained, the software activates one of a plurality of calibration data sets stored in EEPROM to be used for measurements involving the sensors. Eighty-eight such sets have actually been employed.

Calibration strips are plastic slides consisting of printed connecting tracks and resistive bands whose resistance is laser trimmed to a desired value. A calibration protocol is carried out on each new batch of sensors to determine which of the calibration data sets pre-stored in the memory best represents the performance of this lot in the analyte test. Each of these calibration data sets has its own calibration strip with pre-assigned resistance values.

For example, calibration strip 3F may activate column #3 and offset #6 in the calibration database. Each manufactured batch of sensors has an appropriate calibration (or sensor code) strip included to be used for setting up the calibration by the operator.

By inserting the calibration strip into the sensor connector and pressing the START button, the operator confirms that the monitor and the sensors within the lot package function together within the specified measurement bounds of the System. The calibration strips may be reused at any time during the usable life of the lot of sensors in the package.

Self Diagnostics

A sequence of self diagnostic checks is automatically performed each time the device is turned on. The self tests are described in the INIT.SRC section. If any of these tests fails the "ERR" message is displayed on the LCD display and the system is halted, i.e., the device cannot be operated.

Sensor Connection and Sample Solution Placement Test

A further novel feature of the device is the incorporation of a test to determine whether the sensor, or calibration strip, is properly connected to the electronics via the connector. If a sensor is detected (see Sensor Recognition Test) the sensor connection is monitored continuously (at one second intervals) during the test sequence. In the event that an improper sensor connection is detected, an instruction "CHECK SENSOR" is displayed on the Monitor's LCD display.

The same routine tests whether all sensor electrodes are sufficiently covered by solution of the tested sample. If no resistance due to the sample solution is detected between the electrodes, a "CHECK SENSOR" message is displayed.

Internal "Dummy Sensor" Test

This test is performed after the Monitor is turned on. It checks the A/D and D/A voltage control and other current measuring components of the electronics by running the scan step of the test sequence after connecting an internal resistor network ("dummy sensor") to the electronics. The voltage is scanned between selected voltages and the currents are measured, stored and compared by the software with expected values. Actual voltage scans have included scans between −500 mV and −2 mV. If test fails, a system error message is displayed on the LCD display. This test confirms acceptable performance of virtually all hardware and software components of the system except the connector which is checked in a separate self test.

LCD Display Functions

LCD message selection includes:

- instructions such as "CHECK SENSOR" and "CALIBRATE"
- warnings such as a battery icon displayed when a low battery status is detected, "ERR: for system error, etc.
- test status displays including "SELF TEST," "READY", and "TEST."

Beeper Functions

The Monitor system supports a beeper which provides an additional way of signaling to the operator that, for example, a sensor is connected improperly or that the test is completed.

RS-232 Interface

Computer and printer communication functions have been implemented via a built-in RS-232 interface and fully supported by the software. The interface allows direct sending of test results to a printer for a hardcopy printout of test. Also, with the use of a PC computer program, the operator can download new test parameters to the research version of the device and upload the measured current data and results.

In production versions, the device supports an RS-232 protocol in a read only format that permits external transfers of selected data from the device.

Software Functions for Improving S/N

The signal to noise (S/N) characteristics of the measurement may be improved by:

- signal averaging; four measurements;
- digital filtration of the forward and reverse currents;
- digital filtration of the difference current obtained by subtraction of filtered forward and reverse currents;
- baseline subtraction before peak measurement (see paragraph below), and
- integration of the peak signal.

Baseline Subtraction Routine

Yet another novel and important feature of the software associated with the disclosed device is the significant simplification of measurement of peak-shaped electrochemical signals. This allows full automation of the data treatment process.

The analysis routine works by detecting two minima, one on each side of the peak, drawing (i.e. calculating) a line through the minima, and then subtracting that line from the curve to remove the baseline offset.

The two minima are chosen by limiting the range that the software searches. A low range is defined on the left side of the peak and a high range on the right. Within this range, minima are found and used to calculate the baseline. The routine works best when repeated to further improve results. The software performs the analysis in four steps:

a) Find the low point in the two ranges, before and after the peak;

b) calculate the slope of the line drawn between these two points;

c) subtract this baseline's value from the data;

d) repeat 1 through 3 above to improve accuracy.

Battery or AC Power Module Operation

The monitor preferably operates as a stand-alone unit powered by a battery or a DC power module. The system recognizes whether a battery or an AC power module powers its electronics. When both AC module and the battery are connected, the system disconnects itself from the battery to prolong the battery's life time.

Battery Saving and LCD Display Burnout Protection

After 10 minutes without activity when battery powered or after 1 hour when AC power module is used, the device functions are turned off to save battery and prevent burnout of the LCD display.

BRIEF DESCRIPTION OF THE DRAWINGS

So that the manner in which the herein described advantages and features of the present invention, as well as others which will become apparent, are attained and can be understood in detail, more particular description of the invention summarized above may be had by reference to the embodiment thereof, which is illustrated in the appended drawings, which drawings form a part of this specification.

DETAILED DESCRIPTION OF THE PREFERRED EMBODIMENTS

Figure 1:
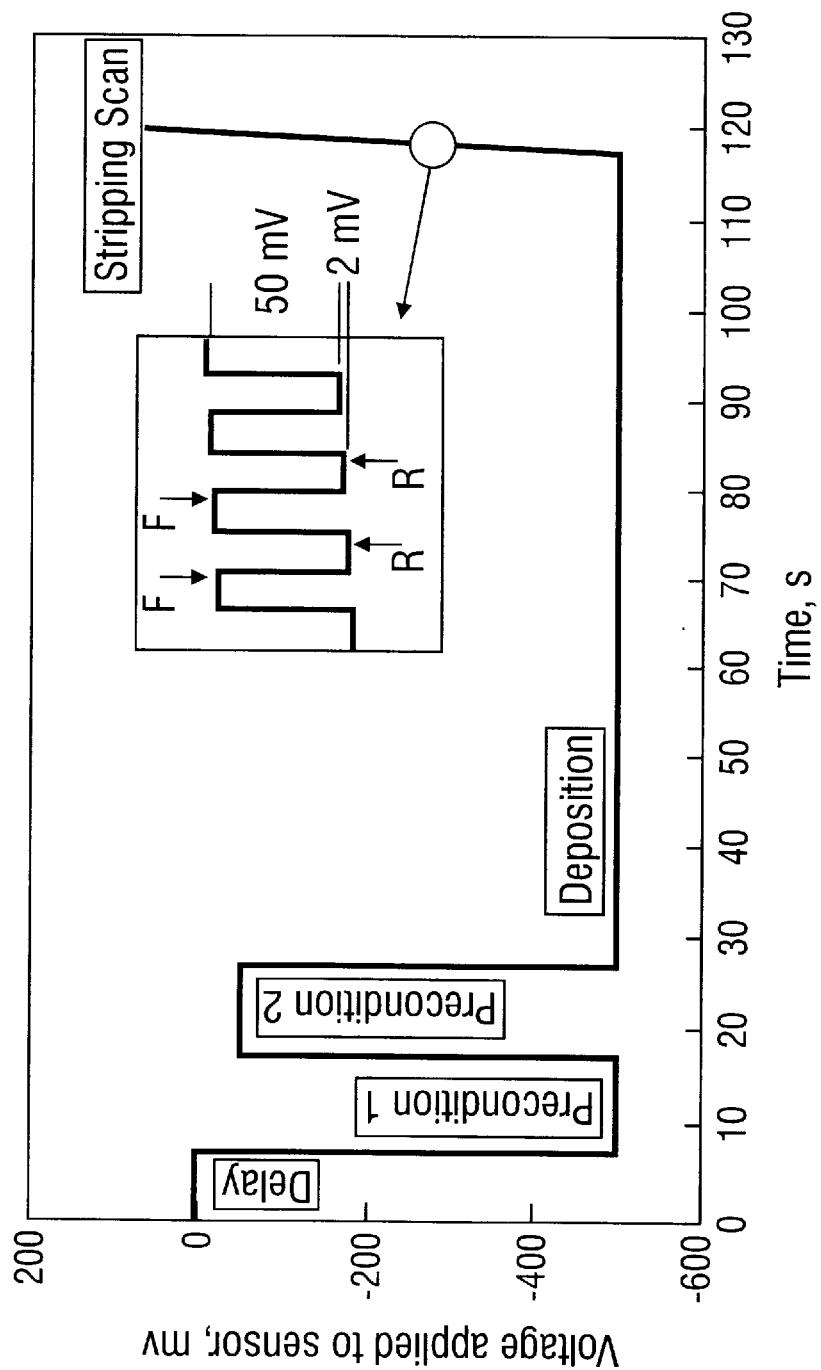
FIG. 1 shows an example of the potential waveform and the current sample scheme used with the invention for anodic stripping measurement. This example is specific to signals for lead in acid treated blood using colloidal gold sensors. "F" and "R" represent the sampling points of forward and reverse currents respectively.

The invention relates to an inexpensive, easy to use and portable electronic apparatus for tests employing disposable electrosensors. The microprocessor based device performs various tasks associated with the measurement of current responses generated by metal ions and non-metal analytes on different kinds of disposable sensors and electrodes. It can be also used to carry out electrochemical measurements using conventional, reusable electrodes and electrochemical cells. The electrochemical functions and techniques available include:

electrochemical preconditioning of the working electrode by potential steps (pulses), amperometric measurements at a constant potential applied to the working electrode, square wave anodic stripping voltammetry, and square wave voltammetry.

The amperometric mode may be used for measurements involving immunosensors, DNA probes and other enzyme based sensors such as colloidal gold sensors for hydrogen peroxide, atrazine, fertility hormones, cholesterol and others. The square wave anodic stripping voltammetry has been used for measurement of heavy metals in biological fluids and environmental samples. For example, operation in this mode has been successfully used in the LeadCare™ Test for detection of blood lead using colloidal gold sensors (AndCare, Inc., Durham, N.C.). The same mode of operation can be used for measurement of lead, cadmium, copper, zinc and other metals in waters and other environmental samples. The technique of square wave voltammetry can be used to measure analytes that do not require deposition (preconcentration) on the surface of working electrode. For example, the device can be operated in the square wave voltammetric mode for measurements of acetaminophen in aqueous samples.

The device is a three-electrode potentiostat employing an auto current gain switching function which allows a much more rigorous control of the potential applied to the working electrode during the entire measurement. This feature improves the S/N characteristics of the device. The device can operate powered by a 9V battery or a DC power module.

The device is a versatile, yet simple to use instrument. It can be used as a stand-alone for conducting repetitive tests involving the same type of sensors and one set of operating parameters. In this mode all the parameters are preset either by the device manufacturer or by means of a calibration/setup microchip "button," and the monitor has only one mode of operation. Similar electrochemical devices available on the market require complicated setup procedures. The measurement is initiated when the operator presses START key after inserting the sensor in the sensor connector and placing a drop of tested sample on the sensor. At the end of measurement the test result is displayed on the LCD display. This can be regarded as a "black box" mode of operation since the user does not have to be familiar with the operation of the device or with the electrochemistry involved in the measurement process.

The same device, can also be used as a flexible instrument for development of electrochemical tests and for other applications involving disposable sensors or other electrodes. This type of operation is designed for more experienced users and requires a control program and a computer connection. The program provides full control of the functions including changing the type of measurement (amperometric, square wave voltammetric, etc.) and/or including the operating parameters. The measurement data can be uploaded from the device to the program for display, analysis and storage in the computer memory.

A sequence of self diagnostic checks is automatically performed each time the device is turned on. If any errors are detected in the hardware or software, an error message warns the user. Also, the battery status is checked continuously and a battery low icon is displayed if the battery voltage drops below 6.8 V a selected voltage—for example, 6.8V with a 9V battery. When the battery voltage is 6.4 V or less, the device will shut down all its functions. Sensor connection and sample drop placement are tested automatically at the beginning and during the test. In case the sensor is not connected correctly, or the sample does not cover completely the electrodes on the sensor, or the sensor accidentally is disconnected during the test, "CHECK SENSOR" is displayed on the LCD display and the measurement sequence is aborted.

A temperature correction function may be added to correct for the temperature dependence of the entire test process, including the diffusion of electroactive species at the electrode surface. It is based on a thermistor probe mounted on the circuit board and controlled by the microprocessor unit (MPU). The temperature is measured before and after the test and the test result is extrapolated to the temperature of 25 degrees Celsius using temperature correction database stored in the EEPROM. This function eliminates errors due to variations of the temperature of tested samples.

Sensor preconditioning function involves a set of four independently controlled steps (pulses) that can be used for electrochemical preconditioning of the sensor. Each preconditioned step can be set for 1 to 600-second duration and the applied potential from the −2000 to +2000 mV range. These steps may be used without potential applied to the sensor to aid the operator in controlling the time of other steps in the test procedure. Potentials applied may be changed gradually between the preconditioning and measurement steps which very often helps reduce the charging stress on the electrode surface.

The sensor housing is a novel device designed to stabilize the temperature of the sample solution on the sensors and thus reduce the effect of solvent evaporation on the current signals measured using sensors. This add-on module attaches to the sensor connector. The housing consists of a plastic part and an aluminum plate forming its bottom. The slot into which the sensor is inserted forces the bottom surface of the sensor to slide over the aluminum plate and lay down firmly on its surface. The aluminum plate functions as a heat sink preventing the cooling of rhe sensor as the water evaporates from the tested solution. The evaporation effect is particularly significant for the measurements conducted in dry environments, e.g., at relative humidities below 40%. The sensor housing also creates a draft screen for the tested sample which substantially reduces the effect of evaporative cooling caused by draft. The sensor is first inserted half way into the housing so that the electrode area on the sensor is above and over the aluminum plate. The tested sample solution is deposited and spread over the sensor electrodes. The sensor is then pushed all the way to the end of the housing and into the connector. This motion engages the contact between the sensor contact tracks and the connector springs.

The disclosed microprocessor based instrument is designed to perform various tasks in the measurement of analytes, such as metal ions in biological and environmental samples. The instrument advantageously operates as a stand-alone unit powered by a battery or a AC power module, and is equipped with a communication port that allows uploading analytical data to a computer. The unique electronic, microchip, and software configurations developed for this device, have made possible a portable, low-cost, safe, automated, and simple to operate instrument that is capable of precise and accurate measurement of a wide range of analytes, including metals, peroxides, glucose, proteins, drugs, pesticides, etc.

The innovative design of the disclosed apparatus incorporates a new data processing method for extracting analytically useful signals from anodic stripping currents. In certain embodiments, the apparatus preferably employs a colloidal gold based electrode that allows high sensitivity of detection of analytes so that exceptionally low levels of analytes may be detectable.

An important feature of the present invention is the sensor lot calibration scheme. The disclosed device may be set up for tests using different lots of sensors thereby eliminating complicated and time consuming manual calibration strip procedures required by other devices on the market attempting to perform similar analyses. There are two general designs used in the devices for the calibration; one involves storage of specific calibrations in the apparatus; another alternative and more versatile embodiment allows calibration data specific for the sensor to be loaded into the apparatus prior to an analysis.

The first version uses a calibration scheme that involves a resistor network-based calibration strip and sensor calibration database stored in memory. It does not require any user intervention except insertion of the calibration strip and pressing the START button. The device recognizes that a calibration strip, and not a test strip, is connected and conducts a measurement of resistance of two resistors on the strip. Based on the two resistance values data from one of the calibration curves stored, the EEPROM is transferred to the active portion of a lookup table. Until another calibration strip is read, this data is used by the device to convert measured signals to the concentration of analyzed species.

In a preferred embodiment, a novel version of a sensor lot calibration scheme is employed that also allows setting up the operating parameters for a particular test in which the sensor is used. It involves using a microchip, herein referred to as a "Calibration Button," to store and download the calibration data and other data coresponding to a lot of sensors that will be used in the test. A digital microchip reader of a size of a nickel coin is mounted on the device that enables data transfer. Each lot of manufactured sensors will have a unique Calibration Button, and such a chip can be included with each set of sensors sold from the lot.

To prepare the memory chip, one may use a programmable memory chip such as Dallas Semiconductor's Touch Memory. 1K (64 data words), one time programmable memory chips and programmable 4K memory chips are suitable. In one version of the button, a 45-point calibration data set, a 7-point temperature correction data set, and the sensor lot code and production date, in addition to the microchip ID code were stored. Another version of the button sets up the device to a desired operating mode (amperometric or square wave, for example) and changes the operating parameters, including calibration, for the test and sensors to be used.

A memory reader probe, mounted on the enclosure, is used to transfer the calibration data to the lookup table stored in the memory. When the device is in the READY mode, the Calibration Button reader is in the active mode and ready to sense the attachment of the Button. The transfer is executed when the user connects ("touches") the button to the reader and the electromonitor device recognizes that a Calibration Button is attached and ready for transfer of calibration data. Unlike the earlier described resistor based calibration strip, the START key is not involved with the use of Calibration Button. Transfer of data from the Button to the device takes less than 1 second.

Memory touch types of programmable chips are inexpensive and one calibration button can be included with each set of sensors sold. Although the 1K version is preferred, the sensors may also be developed with a programmable 4K button. This allows storing calibration data stored in the button's memory chip multiple times using a computer program. Programming of the buttons is fast; much less than 1 second per button. Buttons may be purchased and no extra labor, except programming and labeling, is required. For certain applications, this presents an advantage over the calibration strip approach which requires more elaborate and timely coordination of efforts between the sensor producer and the monitor manufacturer.

The following material discusses the software and the hardware used in the instrument. A brief overview describing the method utilized in the measurement is presented first.

Method Overview

The electronic device of the present invention measures an electrochemically generated signal from an analyte in a drop of solution placed on a disposable sensor. The instrument executes a sequence of voltage steps (voltage pulses) that are applied to the electrodes on the sensor (FIG. 1). The electromonitor measures currents generated by the sensor during the analysis. It then numerically processes these currents to determine the analyte signal. In the final stage of the test, the electromonitor converts the analyte signal to a corresponding analyte concentration in appropriate units and displays the result on an LCD display.

The electroanalytical techniques on which the operation of the electromonitor is based are square wave coulometry (SWC), anodic stripping voltammetry (ASV), and amperometry. The SWC can be characterized as a hybrid of three electrochemical techniques: Anodic stripping voltammetry, square wave voltammetry, and coulometry. The electromonitor can apply the appropriate analytical technique to measure signal for a selected analyte. Because this measured signal is proportional to the concentration of analyte in solution on the sensor, a simple conversion of this signal to the corresponding analyte concentration can be performed using calibration data loaded in the memory of the electromonitor.

Hardware Overview

Figure 3:
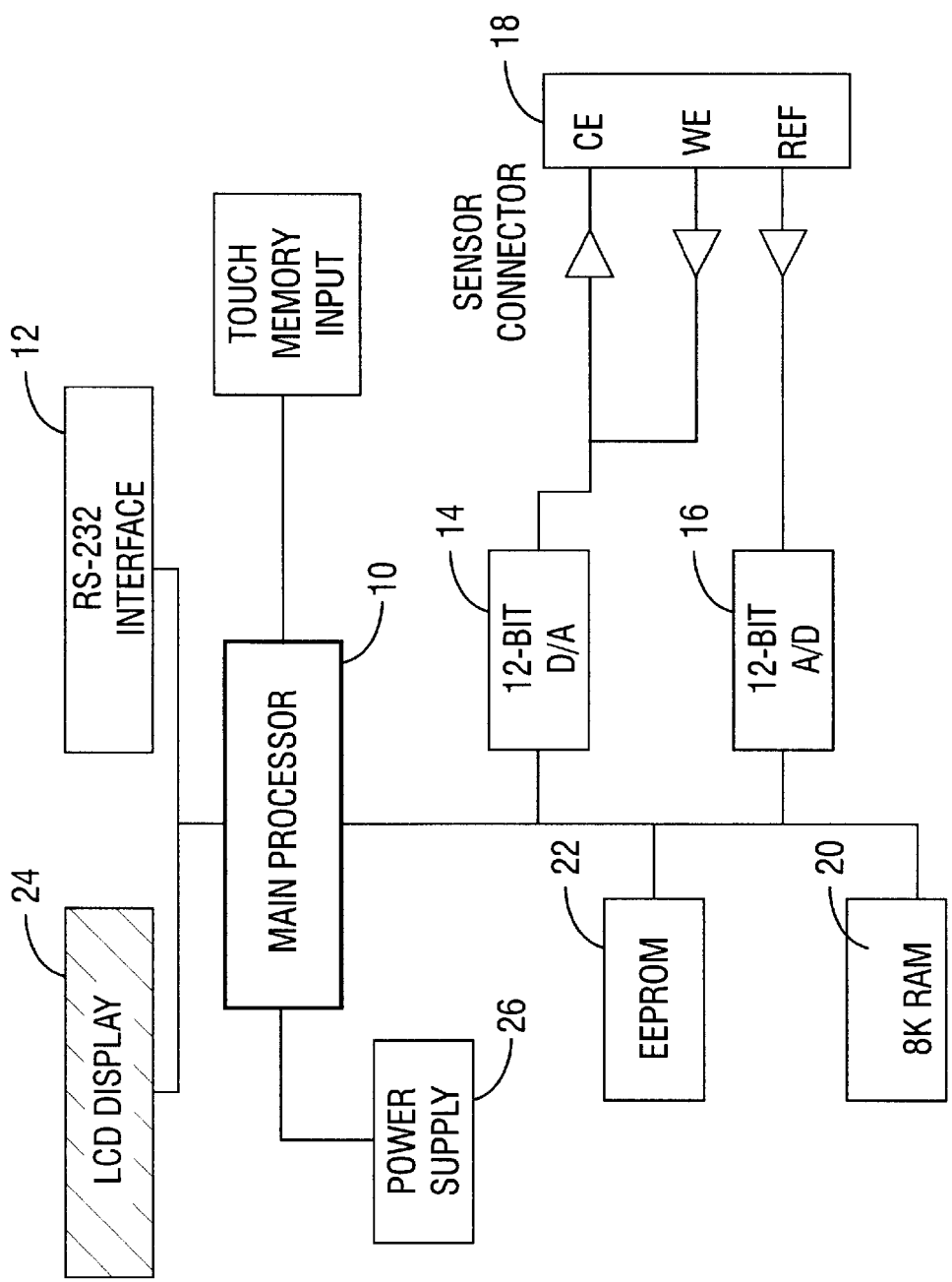
FIG. 3 is a flowchart of various hardware component blocks that comprise a device of the invention.
Figure 8:
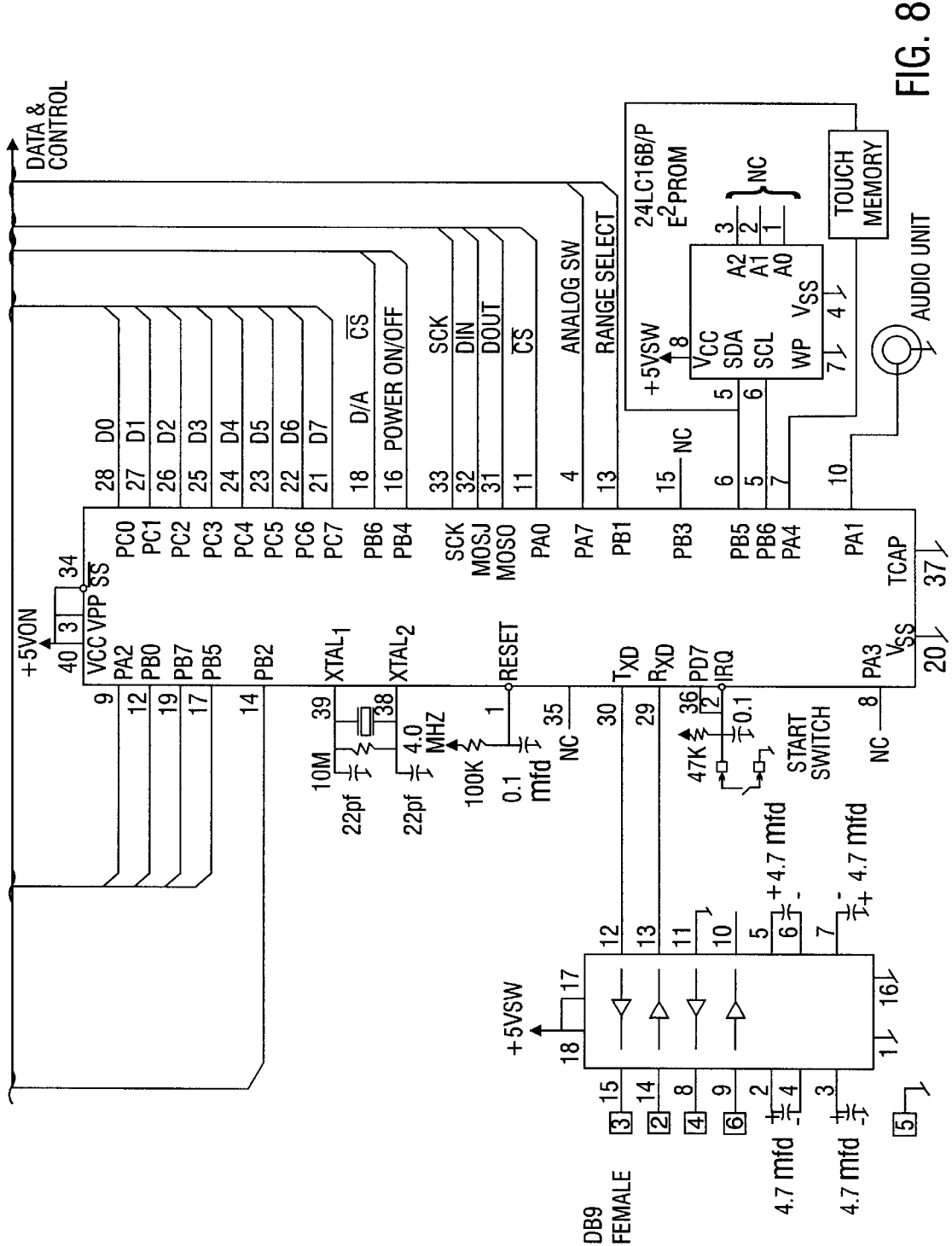
FIG. 8 is a schematic diagram of an exemplary microprocessor system. The exemplary diagrammed system is built around a MOTOROLA MC 6805 main microprocessor which is 8 bit with 176 bytes of internal RAM, 8K bytes of program memory space, 24 I/O lines, 2 serial interfaces, and a hardware timer.

The block diagram of the system shows the basic hardware elements (FIG. 3). The system in one embodiment may be built around a MOTOROLA MC6805 main microprocessor 10, see also FIG. 8. The MC6805 is an 8 bit microprocessor with 176 bytes of internal RAM, 8K bytes of program memory space, 24 I/O lines, 2 serial interfaces, and a hardware timer. The 24 I/O lines and one serial port are used to connect to the external components. The second serial port allows a host computer to communicate with the system using a standard interface such as the RS-232 interface 12.

Figure 9:
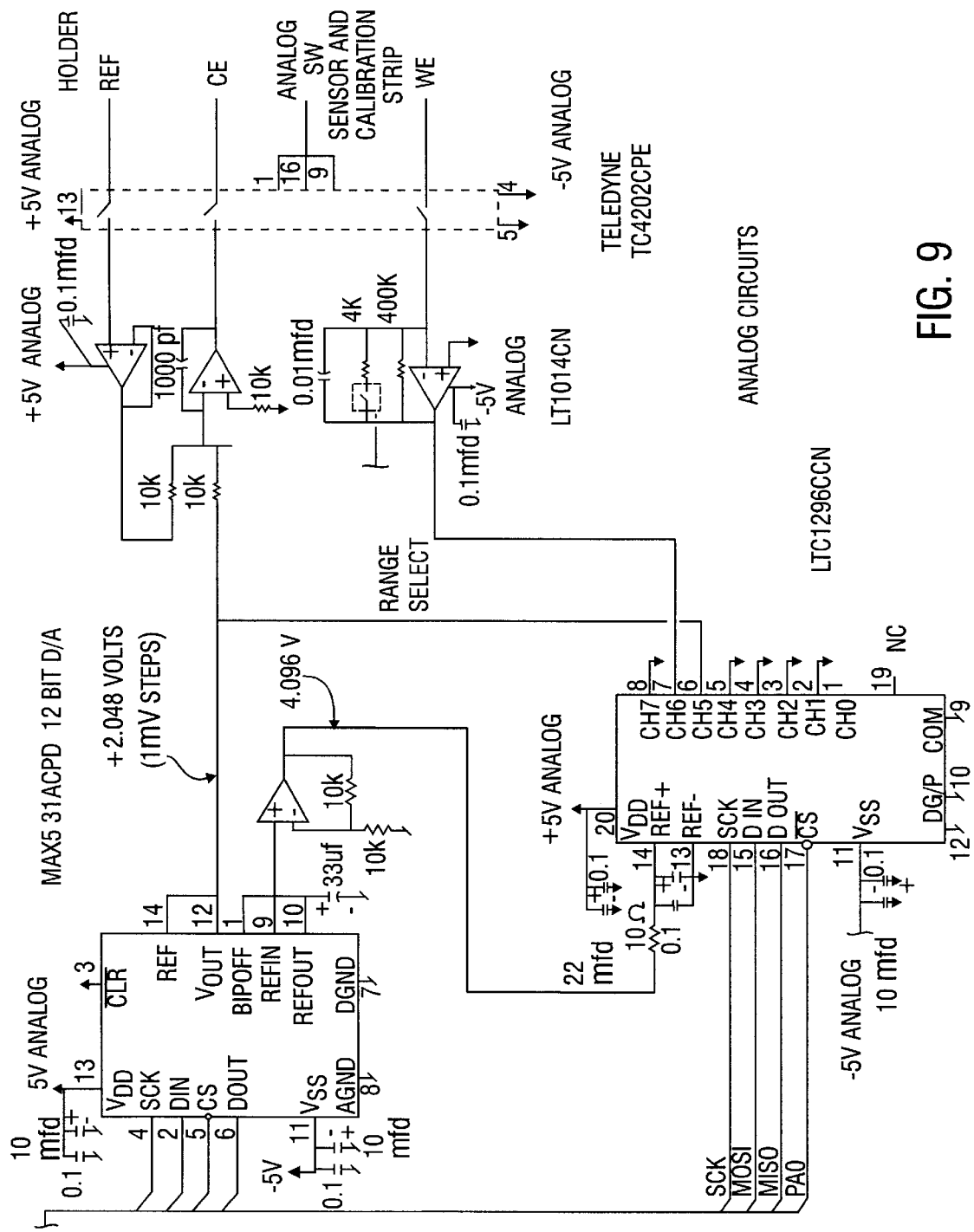
FIG. 9 is a schematic diagram of an exemplary analog circuit which includes a digital-to-analog (D/A) converter to generate a known voltage and an analog-to-digital (A/D) converter to measure the current.

The analog circuit (FIG. 9) includes a digital-to-analog (D/A) converter 14, (FIG. 3), to generate a known voltage and an analog-to-digital (A/D) converter 16 to measure the current. Additional Op Amps generate the counter electrode voltage and measure the reference voltage of the sensor and convert the current to a voltage for the A/D. An analog switch allows disconnecting the electronics from the sensor connector 18 when no sensor is installed.

Figure 10:
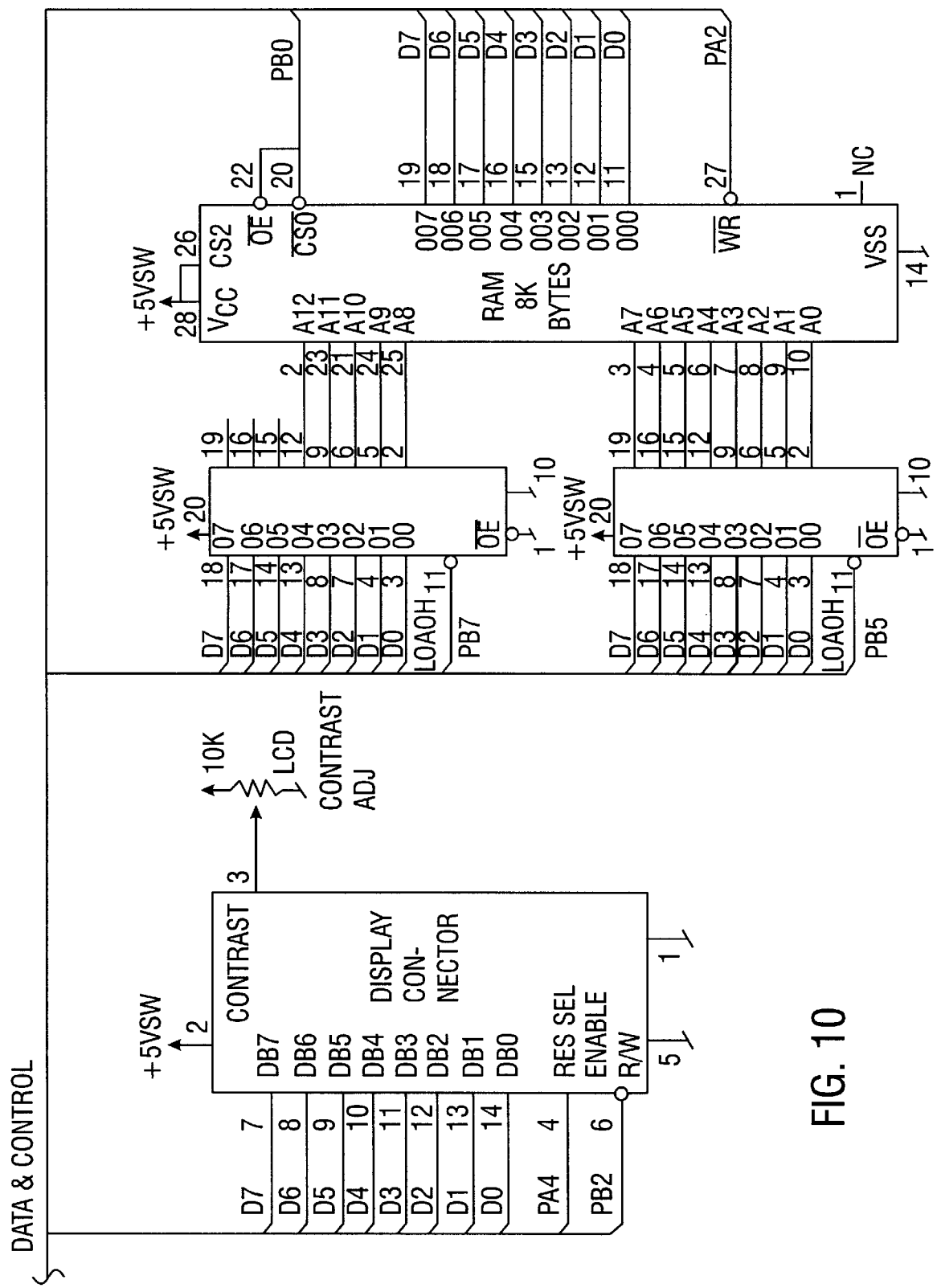
FIG. 10 is a schematic diagram of an exemplary display/memory system which stores parameters for the measurement process and data collected while processing the sample.

The data collected while processing the sample is stored in an external 8K byte RAM 20 (FIG. 10) for later analysis by the software. An EEPROM memory 22 may be used to store the parameters for the measurement process. A lookup table, if incorporated into the device, translates the result to the final displayed value in display 24.

Figure 11:
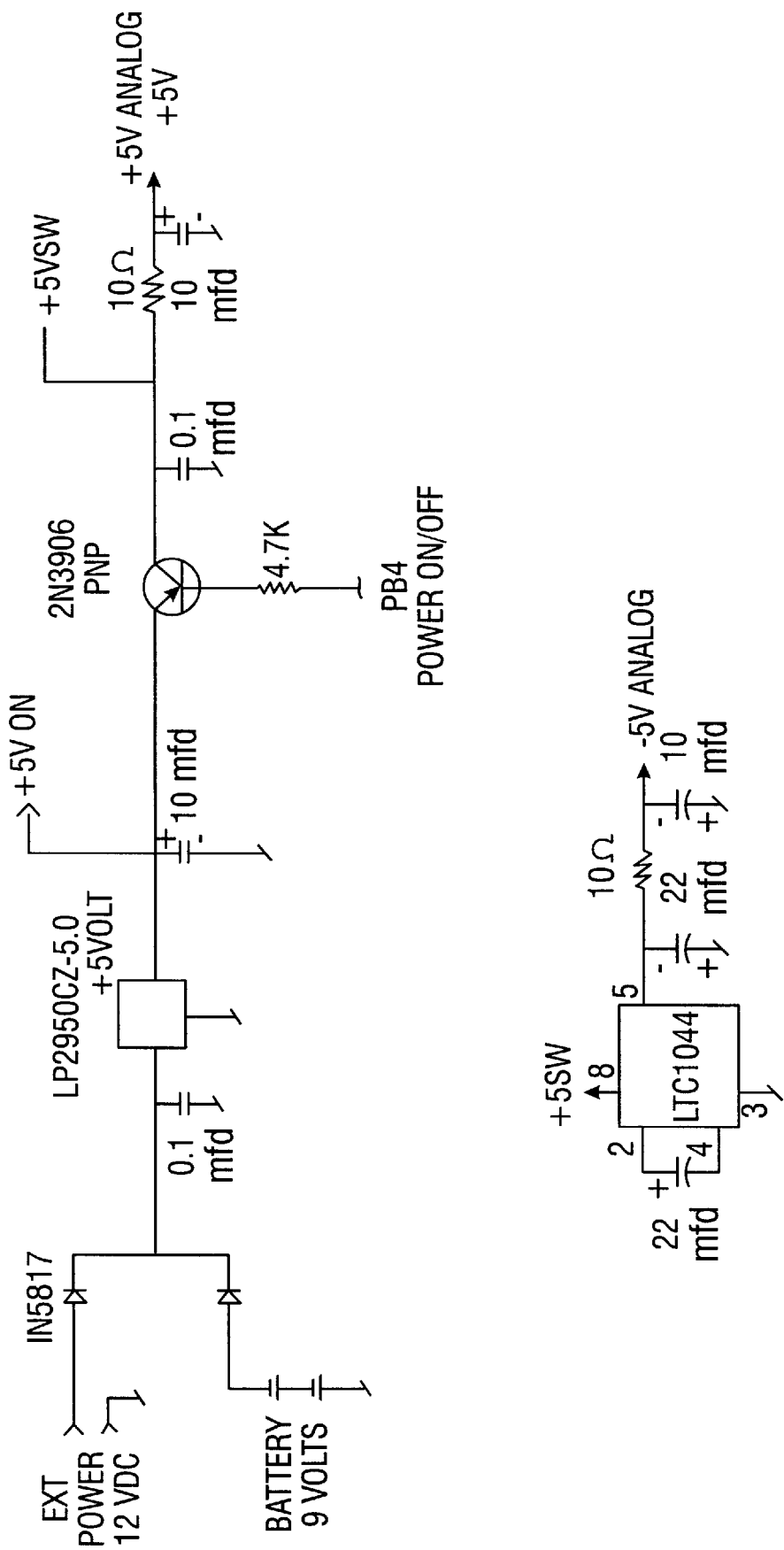
FIG. 11 is a schematic diagram of an exemplary power supply which typically supplies power either by internal batteries or 120V AC power.
Figure 12:
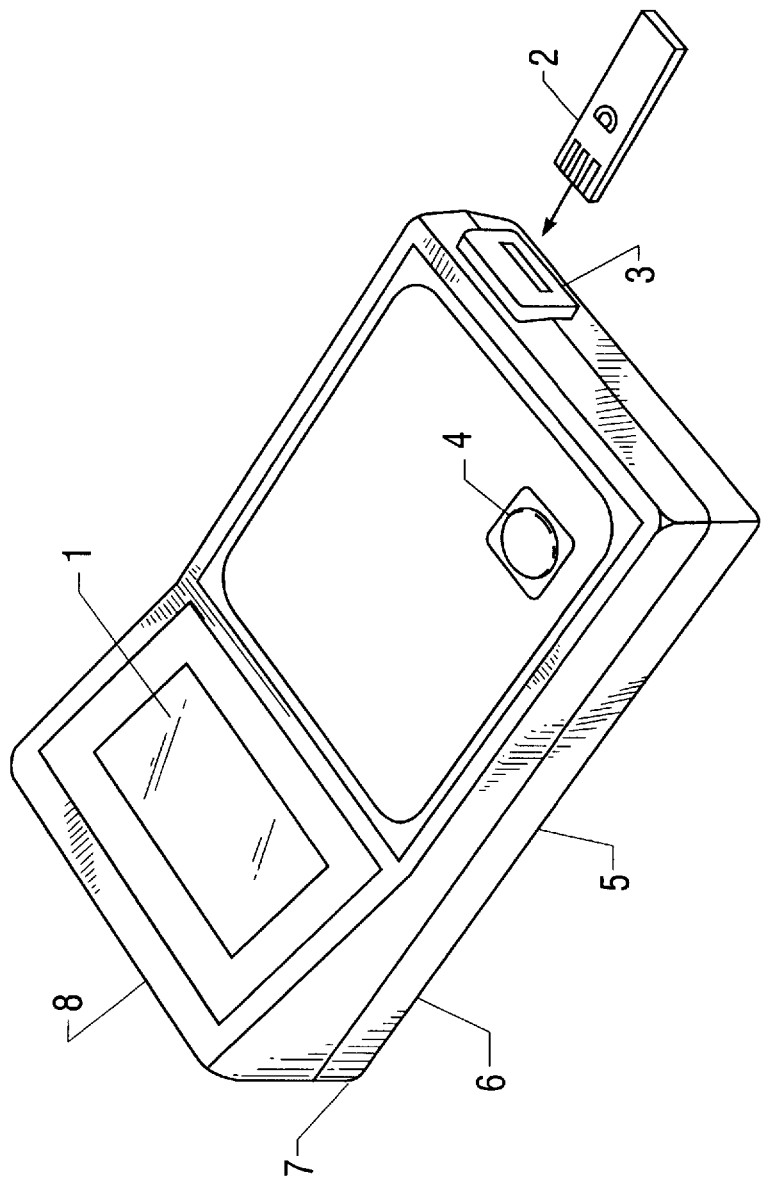
FIG. 12 illustrates a version of an exemplary hand-held electronic monitor indicating the slot where the electrode strip is inserted and where a calibration unit for the manufactured electrode strip may be inserted to connect into the circuit controlled by the firmware. A battery compartment, alternate AC power supply connection, and connector for optional mating with externally supplied calibration programs are indicated.

A power supply 26 for the system (FIG. 11) is provided either by internal batteries or a 120V AC power module. A commercial 16 character display 24 may be used to display messages and the final result of the measurement.

Software Overview

A support program for the unit allows a user to set the different parameters associated with the process. These include timing and voltage levels for each state and frequency of square wave modulation used in the scan state. In addition, the data may be uploaded from the instrument and displayed.

A hardware prototype was built to provide a platform for the development of the software. A MOTOROLA In-Circuit-Emulator was used to allow testing the code as it was written. The software was broken into individually assembled small modules and then linked together.

In addition, a simulation of the analysis routines was written in BASIC to allow testing different methods for acquisition and analysis of data. This simulation in BASIC was effective for development of one embodiment of the device, the LeadCare™ Monitor used for the detection of lead in blood and was also used for optimization of the LeadCare™ test system which includes special colloidal gold based electrodes used with an electromonitor calibrated and dedicated to lead testing.

Firmware Overview

The firmware can be divided into measurement of the data and communications to the host computer. Used in the context of the present invention and as generally understood by those skilled in the art, firmware refers to the software used as part of the disclosed device; that is, the software that is firmly fixed in the apparatus and which has been especially developed for the embodiments disclosed and described herein.

The measurement of data from the sensor is based on connecting the sample to a voltage source for a fixed period of time and measuring the current. This system has been developed as a general purpose tool; as a result, there is considerable flexibility in the device for adapting to measure a wide range of types of analytes.

Figure 4:
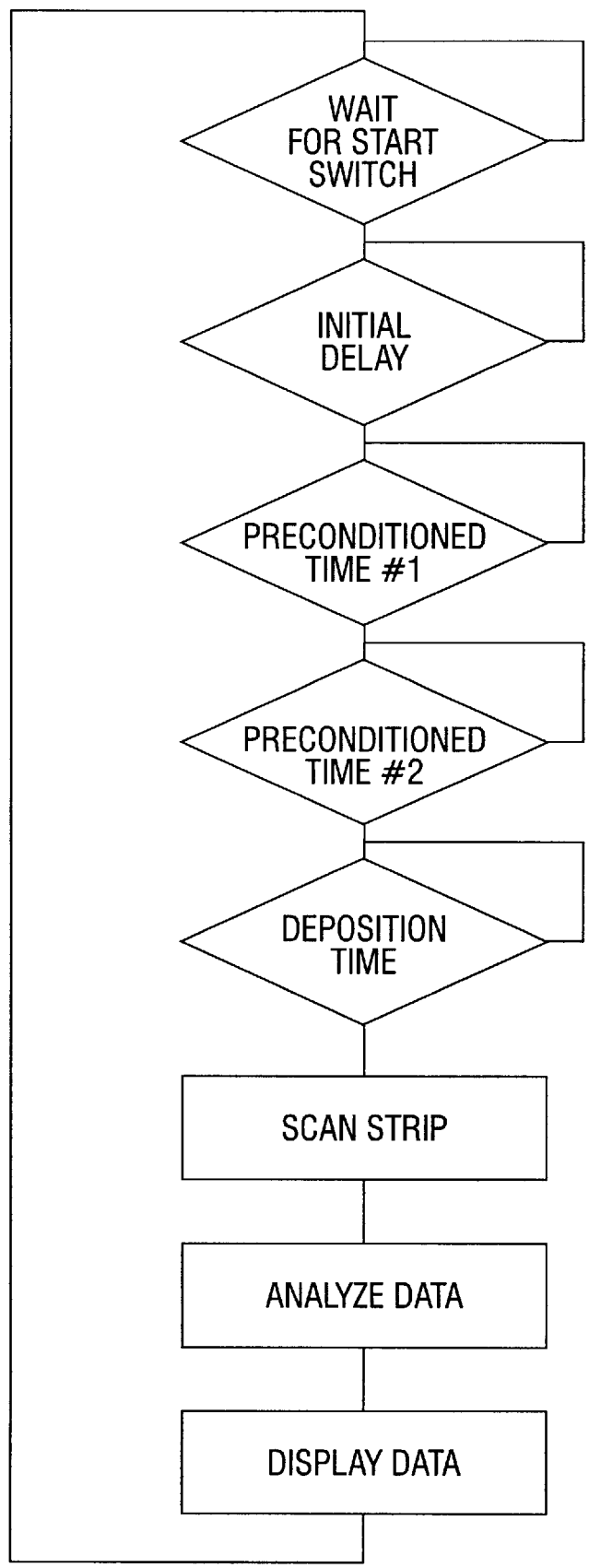
FIG. 4 is a basic firmware protocol for the execution of an entire electrochemical measurement in accordance with the invention.

The firmware flowchart in FIG. 4 illustrates the steps in the process. Each step has an associated time duration set by the user. This time can be set to zero, skipping that part of the process. In addition, each step has a voltage applied to the sensor during that time.

The flowchart shows that the routine starts in a loop, waiting for the "START" switch to be pressed. Once the switch is activated, each step is sequential. If the time is set to zero, that step is skipped. The present system supports 4 stages: Initial delay, Precondition #1, Precondition #2, and Deposition.

The next step is called the Scan stage (see Stripping Scan in FIG. 1). This stage is more complex. The applied voltage is incremented from one level to a final level in a series of steps. During each step, a small offset voltage is applied, first in the positive direction then in the negative direction. During this positive offset time, the current in the cell is measured and stored as the FORWARD current (F). Similarly, during the negative offset, the current is measured and stored as the REVERSE current (R).

Figure 2:
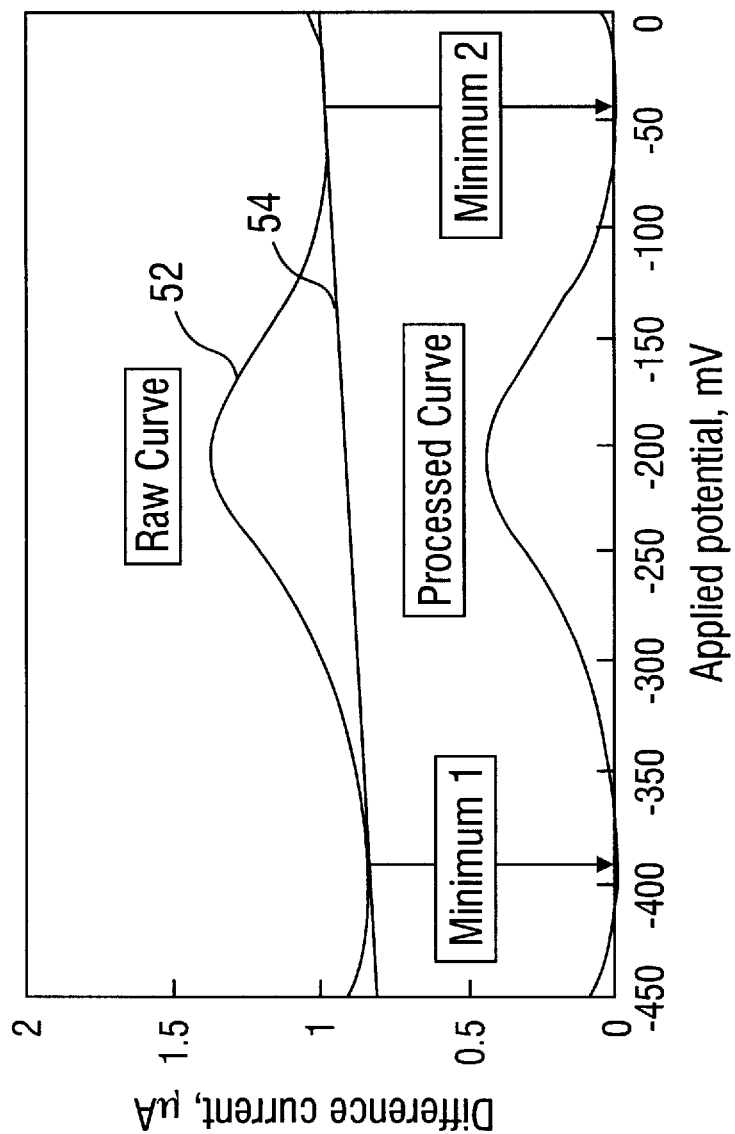
FIG. 2 is a graphic representation of a baseline subtraction procedure used to process a raw electrochemical response into a form used to calculate analyte concentration.

When the scan stage is completed, the data analysis routine calculates the difference between these two currents and using this data, calculates the analyte level (FIG. 2).

The firmware was developed by creating a series of modules which handle one task or function and then linking them together to form the total system. For the purpose of illustration, the modules are grouped into three sections: software framework, data collection and analysis, and support modules.

Software Framework

Figure 5:
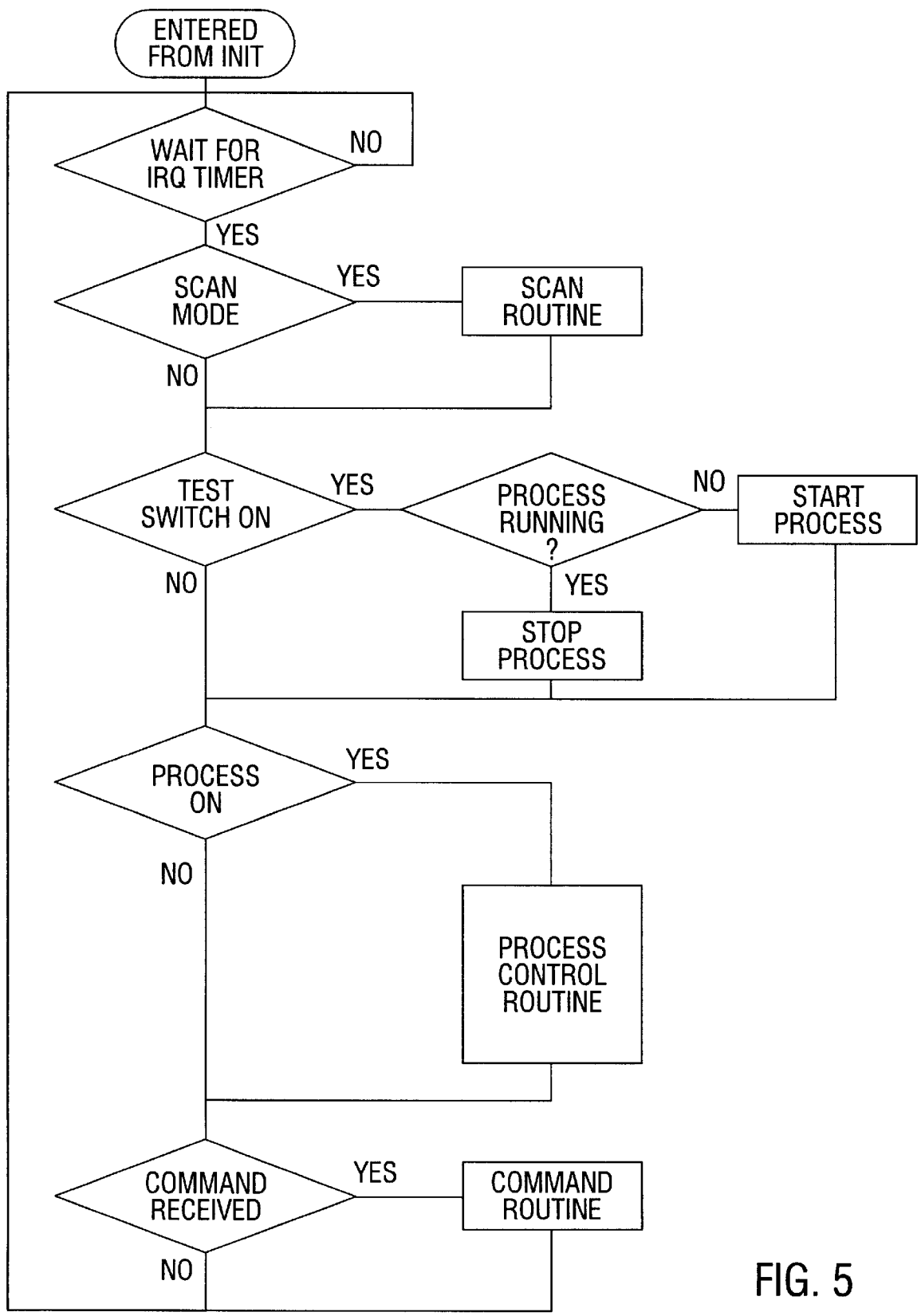
FIG. 5 is a flowchart of a main loop software framework module which directs the invention to poll and wait for signals to perform a certain activity.
Figure 6A:
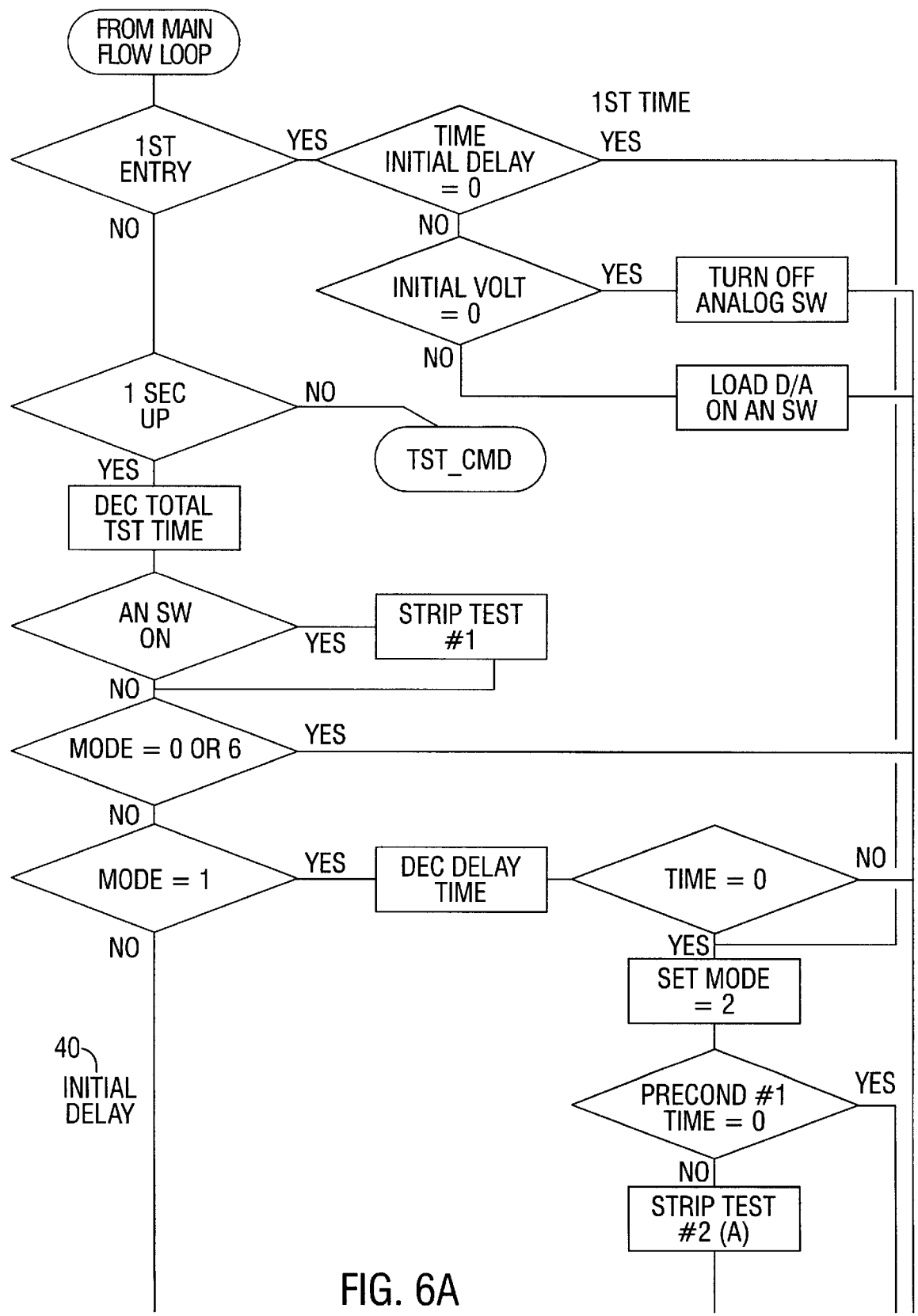
FIGS. 6A–6D is a flowchart of a process control routine which controls the hardware that is connected to the sensor during a test. The sensor test involves applying a voltage to a sensor for a specified period of time.
Figure 6B:
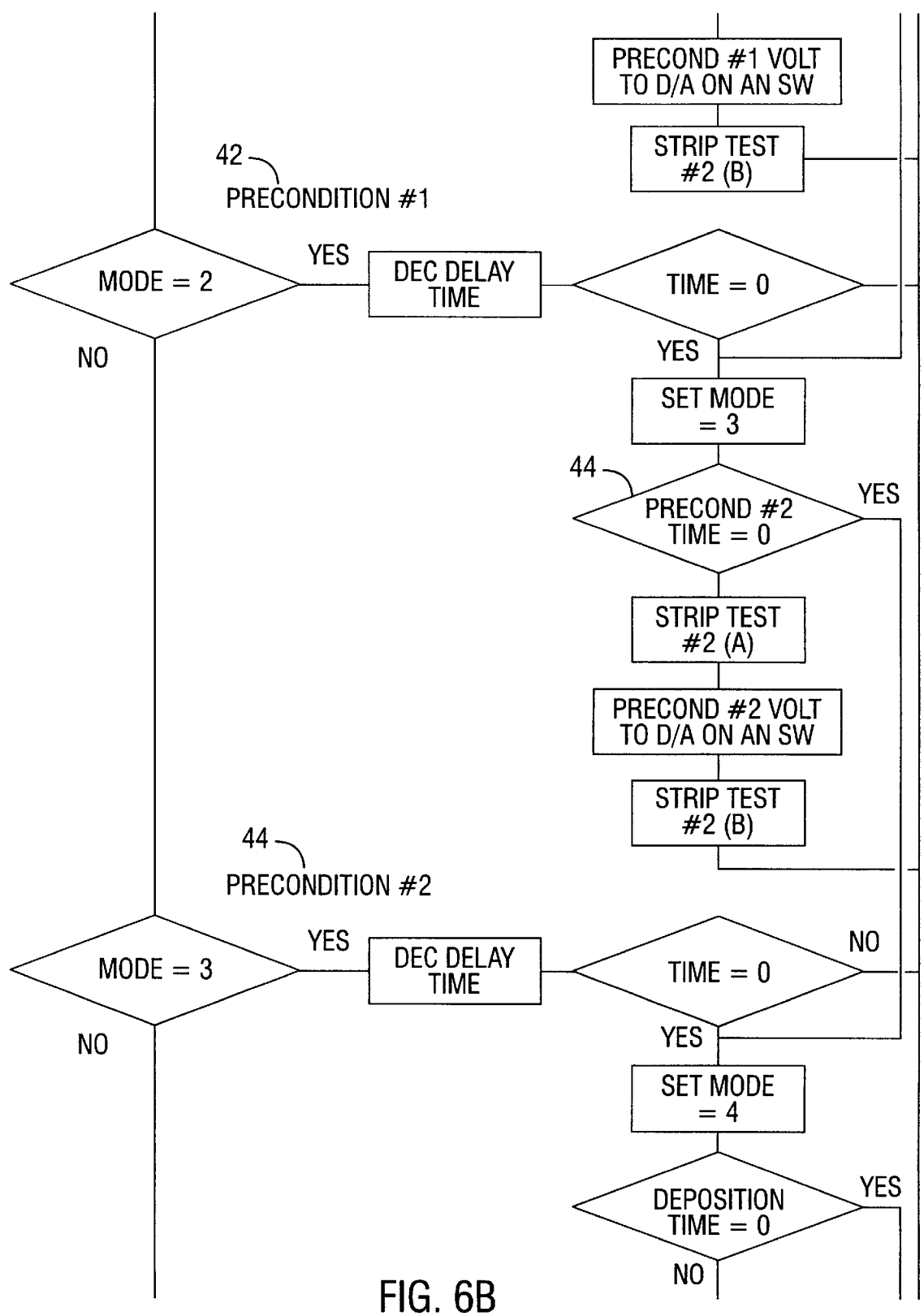
Figure 6C:
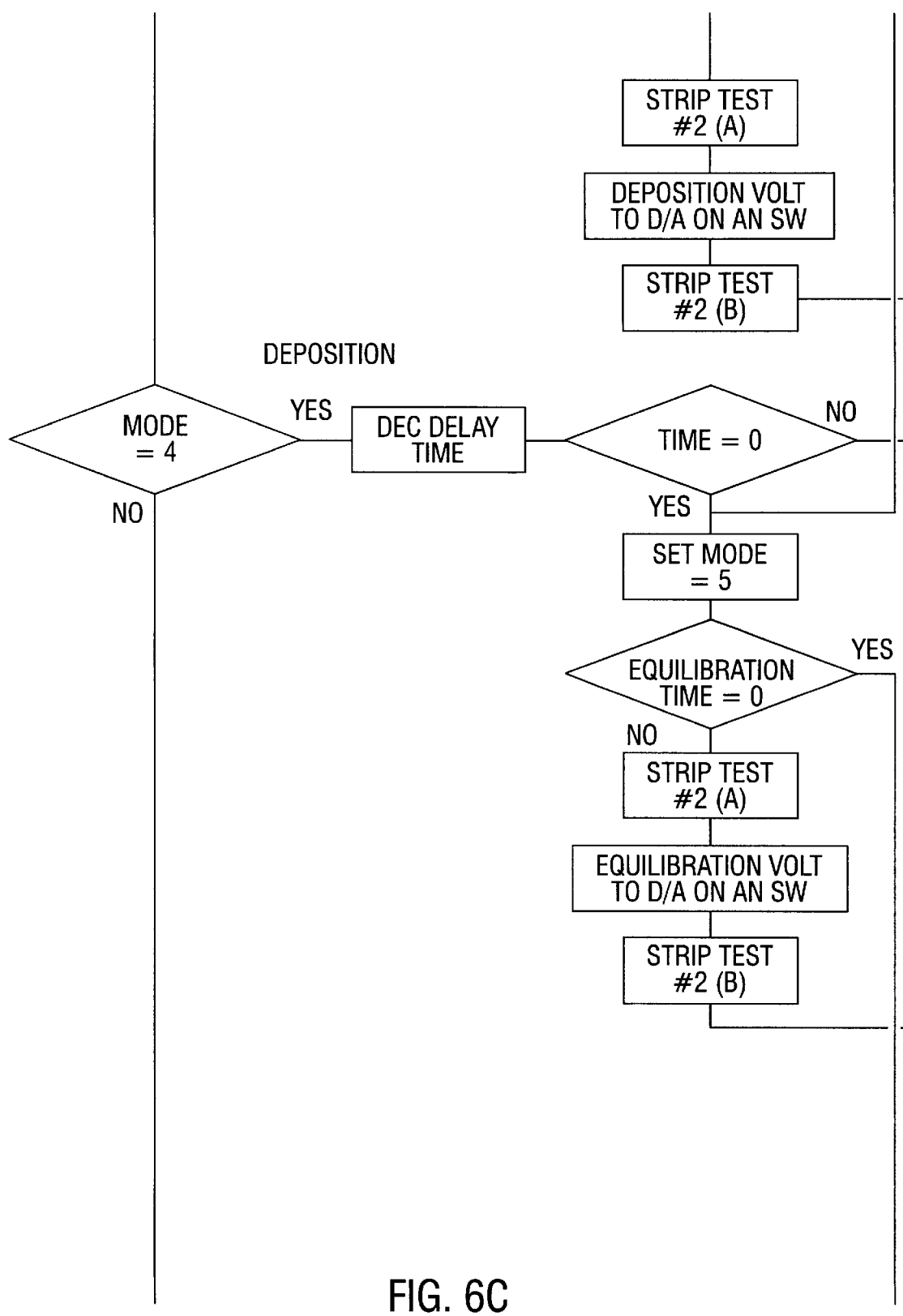
Figure 6D:
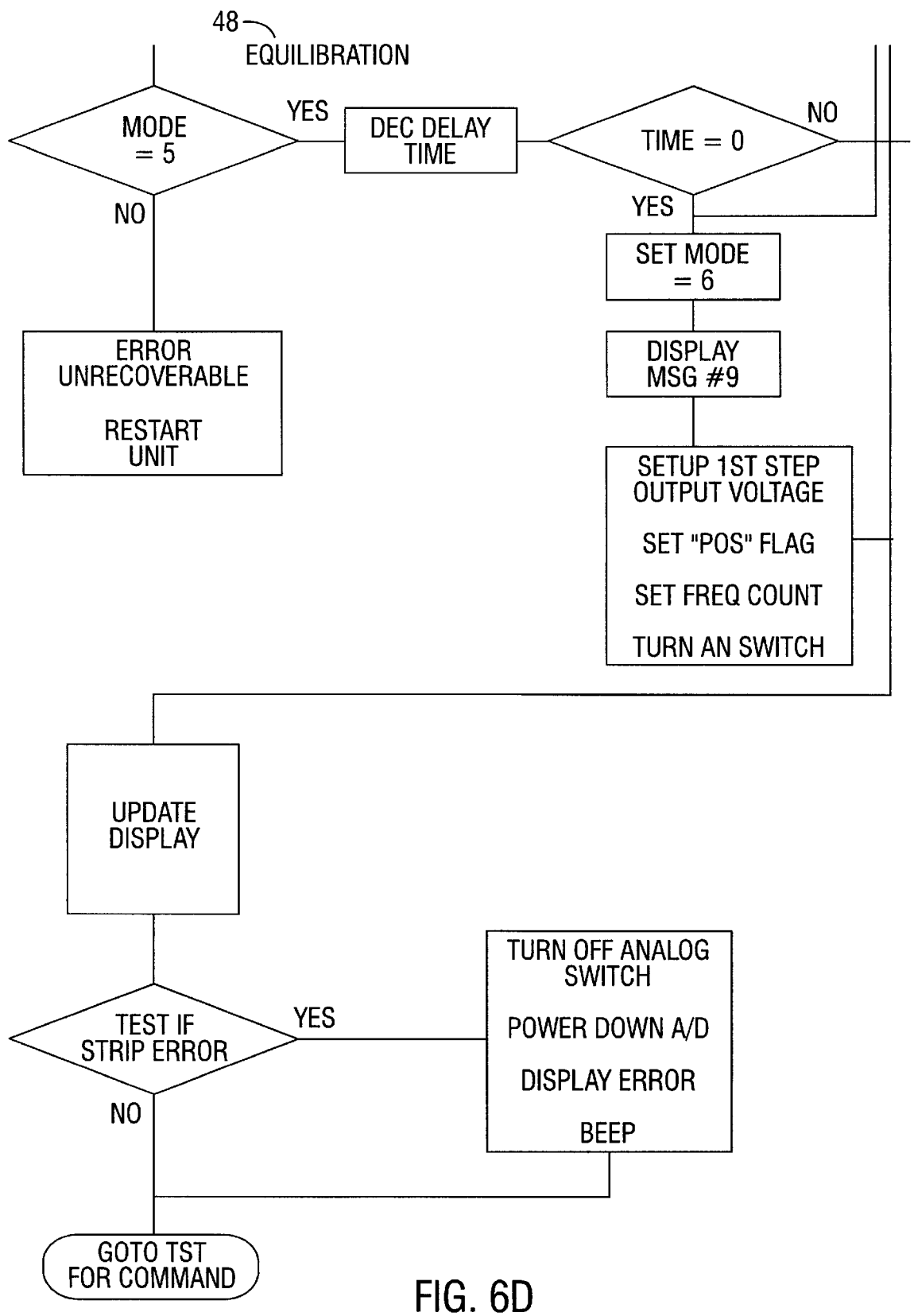

The framework modules make up the program environment. This consists of a main loop (FIG. 5) which polls and waits for signals to perform some activity. When a signal is detected, it exits and runs those modules associated with that signal.

For example, timing is accomplished using hardware in the MPU to cause an interrupt every 5 milliseconds. When this interrupt signal is detected, the firmware module "TIMERIRQ" is run. This module handles the various time parameters such as the timing for the stages during processing.

The framework modules consist of the "INIT" routine which initializes the hardware and software memory, the main control loop in "MAIN" which tests for activities ready to process, and the "TIMERIRQ" routine which provides timing information. Finally, the "VECTORS" module provides support for the MPU interrupts.

Data Collection and Analysis

The firmware which defines the function of the electromonitor consists of seven modules. The first module is in "MAIN." This module contains the basic testing loop. The loop tests the status of the START switch, the status of the process if started, and if any communication requests have been received from the host computer.

If the process has started, additional testing is done to support this mode. This additional testing is primarily to determine if the time is complete for a stage and, if so, setting up the next process stage. The timing is supplied by the basic framework routine "TIMERIRQ" which generates a 1-second signal which decrements the timer for the active stage.

The last scanning stage is handled in the same way. The software for this stage, however, is in a separate module "SCAN" to allow easier testing and modification.

Also, during the initial processing stages, the sensor is tested to determine if it is electrically working. This is accomplished by calling the routines in "STRIPTST" module.

The last four modules analyze the data collected and saved in the RAM buffer. The "FILTER" module first smooths the data collected and calculates the difference values. The "BASELINE" module corrects the data for the baseline offset. (See section on analysis). Finally the result is translated into the correct BLL value using the routines in "LOOKUP."

Support Modules

The remaining modules support the hardware, provide additional math routines and test the system.

| Hardware support routines: | |
|---|---|
| LCD, DISPLAY: | hardware 16 character LCD unit |
| RAM: | hardware external 2K memory |
| EE_CODE: | hardware EEPROM unit |
| ATOD, DTOA: | hardware A/D, D/A |
| SERIAL, SERALIRQ: | hardwareserialRS-232 interface |
| BATTERY: | hardware,measurebatteryvoltage |
| CALCSUM, CHECKSUM: | hardware testing of program memory |
| SELFTEST: | hardware testing of analog circuits |
| STRIPTST: | hardware testing of sensor strip |
| CALSTRIP: | test and measure calibration strip |
| Software support routines: | |
| COMMANDS: | |
| MATH: | software math routines |
| ROUTINES: | software support routines |
| DATA: | |

The firmware performs five internal test routines when started. These routines check the internal and external memory and analog hardware circuits.

The first routine tests the internal memory of the microprocessor unit. The internal RAM memory used to store variables is checked and if an error is detected, the system halts.

The second test checks the internal program memory or EPROM. This is done by calculating the checksum of the internal memory and comparing it to a value previously calculated and stored in memory. If the values are the same, the program memory is acceptable; if not, the system halts.

The third set of tests checks the external memory. The first test checks the EEPROM memory which contains parameters for the test. Again a checksum is calculated and compared with a value stored in memory. If the same, the memory is acceptable; if different, then "SYSTEM ERROR" is displayed. The lookup tables, if used in the device, are also verified and if an error is detected, "SYSTEM ERROR" is displayed.

The external RAM buffer is also tested by writing a fixed pattern to the memory, reading it back and comparing it to the previously written data. If an error is detected, the system displays "SYSTEM ERROR".

The final hardware test checks the D/A and A/D circuits. This is accomplished by outputting a known voltage from the D/A unit and measuring it using the A/D unit. Three voltages are output, −2 volts, 0 volts, and +2 volts. The result has to be within a preset acceptable range. If an error is detected, the display shows "SYSTEM ERROR".

Firmware Module Description

There are 31 firmware modules. A brief description of each is given in the following sections.

DEFINES.SRC

This module contains names of variables and their addresses in memory. The first section contains the hardware locations with the corresponding names used in the software. The remaining section contains variable names with their memory locations.

A 16-bit or 2 byte variable is labeled with an ending of "H" or "L" to indicate high byte or low byte. A 24-bit or 3 variable is labeled with "H", "M", "L" for high byte, middle byte, and low byte.

INIT.SCR

This routine initializes the system when power is first turned on. It is also entered when the system has been powered down and the START switch is pressed to restart the system. This routine performs the following tasks:

First, it initializes the hardware input/output ports, the serial peripheral interface (SP*), the serial communications interface (SCI) and some internal registers.

It tests the internal RAM memory by first writing all ones to the memory location followed by zeros. This leaves the memory reset to zero upon completion.

Next, the routine tests the internal program memory by doing a checksum total on program memory space and comparing this to a prestored checksum value.

If either of these two tests fail, the system will not turn on.

The hardware timer is set to generate interrupts every 5 milliseconds and the interrupt logic is enabled.

The next section of code determines the source of the power for the instrument. If the source is the DC power module input, no battery check is done. If the battery is the source of power, the battery is checked and if low, a flag is set to display "BATTERY LOW" message later. The power source check routine is repeated every minute during normal operation of the unit.

The display is tested by tuning on all segments and activating the beep for 2 seconds.

The calibration strip code is displayed for 2 seconds.

Finally, the display shows "READY." After the START switch has been released, the system goes to the main entry point in MAIN.SRC.

MAIN.SRC

The MAIN.SRC section of code contains the primary system flow loop. This loop consists of a series of questions that are sequenced through to determine which operation should be performed. The loop is run every 5 milliseconds when the hardware timer causes an interrupt and the software exits the "WAIT" command.

The software first tests if the system is processing a sensor and is in the scanning mode. If so, it goes directly to the scanning software routine 30 in "SCAN.SRC" When the routine is completed, it returns.

The next test determines if the process is active. If it is, the process control routine is run (FIGS. 6A–6D). This routine is flow charted and will be discussed later.

Next, the software determines if a command request has been received from the serial port. If one has been received, it goes to the "COMMAND.SRC" routine 34 and processes the command.

Finally, once every minute, the source of power is updated and the software loops back to the WAIT instruction 36 and waits for the next interrupt.

The process control routine (see FIGS. 6A–6D for start) controls the hardware that is connected to the sensor during the test. The sensor test consists of a series of steps which precondition the sensor electrodes by applying a voltage to the sensor for a given period of time. The actual measurement scan is then initiated to collect the data which will be later analyzed and an analyte value determined. There are 3 stages prior to the scan routine: Initial Delay 40, Precondition #1 42 and Precondition #2 44.

Upon entry into this routine, the system determines if this is the first time. If this is the case, it sets up the initial delay time. If the initial delay time is zero, then the system jumps to the setup routine for Precondition #1. If the time is not zero it also checks to see if the voltage is zero. If this is so, the analog switch does not connect the sensor to the electronics. If the voltage is not zero, the analog switch is turned on and the software goes to the exit routine.

Once the first setup routine has been run, the softward loops to the time test. The remaining code is run every second. This is accomplished by monitoring a flag that is set by the timer interrupt routine every second. If the flag is off, the software goes to the test command routine.

If the one second flag is on, the code first tests the electrical connections to the sensor if the analog switch is on. Next it tests which stage is presently running and continues that routine. These routines are all similar. First the time the stage is to be active is decremented and checked for zero. If the time is up, software goes to the setup routine for the next stage. If the time is not up, it exits through the exit mode routine.

The setup routine starts by setting the new mode or stage number. Next it checks the time delay for this stage and, if zero, skips and goes to the next stage.

The first part of the sensor test is next. This test measures the current coming from the sensor and saves the value. Next it outputs a new voltage for this stage. It remeasures the current and compares it with that previously stored. There should be a difference due to the new voltage applied. If not, an error is indicated and the error flag is set. This error flag will be handled in the exit mode routine.

The final stage sets up the scanning mode. It starts by displaying "PROCESSING." Next it calculates a new voltage value based on the last voltage and step size and outputs this to the sensor. Finally it updates the frequency counter and sets a flag to indicate that the direction of current is positive, or forward. If the analog switch is not on, it is turned on.

The exit mode routine occurs next. It checks to see if any error was detected by the two electrical tests of the sensor. If an error is detected, the display shows "STRIP ERROR" and sounds a tone.

SCAN.SRC

Figure 7:
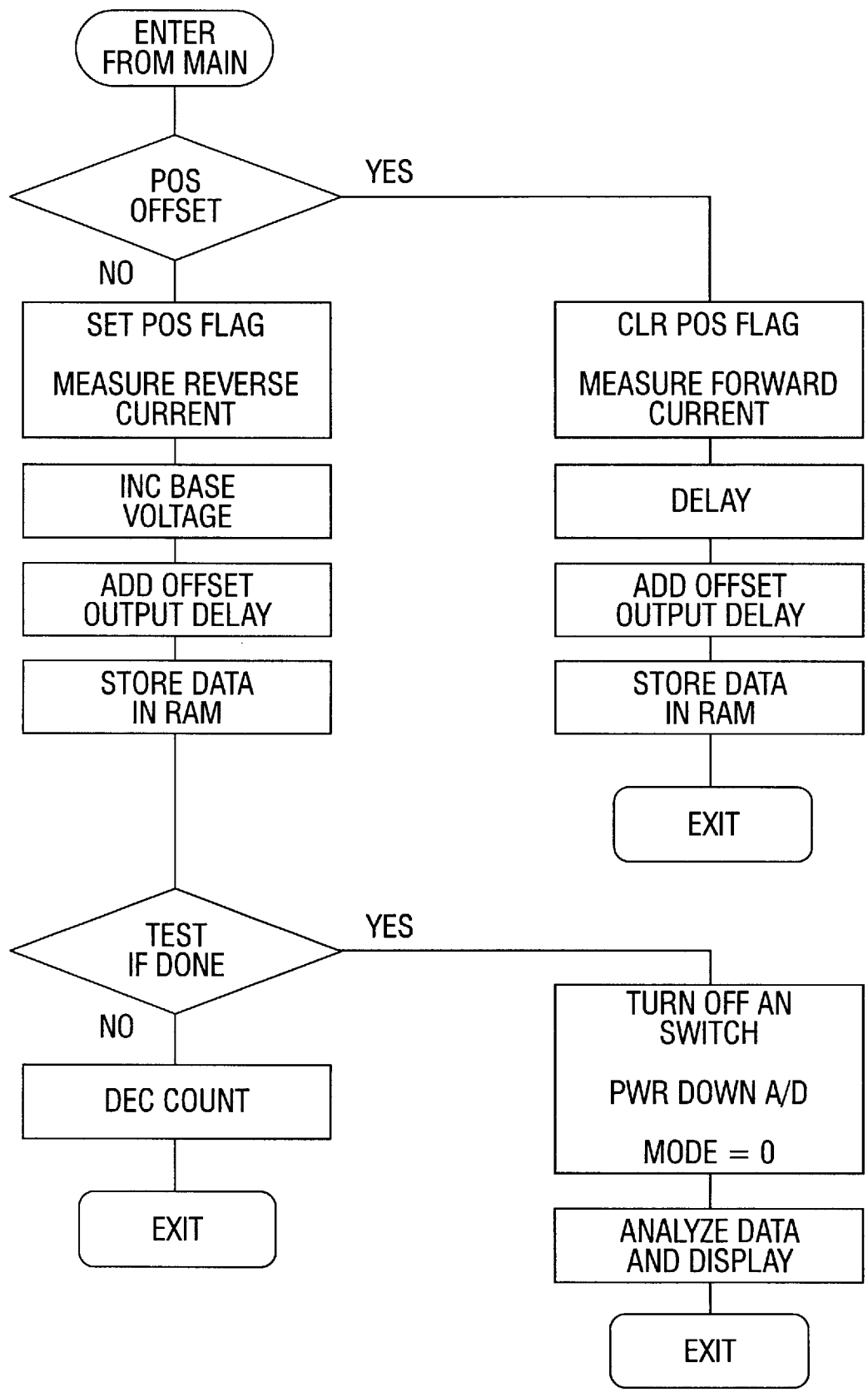
FIG. 7 is a flowchart of a scanning routine which provides the actual data measuring software for the sensor electrochemistry. This routine scans the voltage from a first voltage value to a final voltage value.

The scan routine (FIG. 7) provides the actual data measuring software for the sensor electrochemistry. This routine "scans" the voltage from the last voltage value up to a final voltage in equal steps of 2 mV increments. Given an initial voltage of −500 mV and a final voltage of +50 mV, the software steps the voltage up in 275 steps of 2 mV.

During each step period, based on the frequency of the scan, an additional offset voltage of first +25 mV and then −25 mV is applied and the resulting currents measured and saved. See FIG. 1.

The firmware to do this process consists of two routines, one for the positive offset adjustment and one for the negative. When the positive offset is active, the current measured is called the FORWARD current, and the negative offset current is called the REVERSE current.

The frequency of the scan is determined by the hardware interrupt timer rate which is set at 5 milliseconds and the count in the frequency counter. For a frequency of 50 Hz used the test the count is 2 which makes the period equal to 10 milliseconds or 20 milliseconds for the total square wave cycle.

The current is measured by a subroutine that actually measures the current four times during each half of the square wave cycle and averages the results. This is done to reduce effects caused by noise in the system. The calculation is done using 3 byte variables due to scaling on the A/D results.

The completed measurement is stored in the external RAM for later analysis. The record format in the RAM is as follows:

| N | Forward current |
|---|---|
| N+1 | Reverse current |
| N+2 | Voltage applied to sensor |
| N+3 | Difference current (calculated at a later time) |

FILTER.SRC

The filter routine performs four functions. It filters both the forward and reverse current values in the external RAM buffers. Next it calculates the difference between forward and reverse currents and stores this in the buffer memory. Finally it smooths difference data before analysis.

The filter algorithm is a running average of 8 values. It is easy to divide by 8 simply by shifting the result 3 times to the right. The eight values are chosen with the value of interest in the fourth position.

The routine starts by adjusting the starting and ending pointers so valid data will be used in the averaging process at the two ends of the data table. Next the table is scanned adding up 8 values, dividing by 8 and storing the result.

In calculating the difference, the code scans the memory buffer, subtracting the reverse from the forward current value and storing the result in the last location of the data record.

ANALYZE.SRC

The analysis routine is the most complex of the modules due to the number of math operations. The routine to do the analysis was developed after encountering the limited capabilities of the microprocessor to perform complex calculations.

The data collected by the processor consist of the difference currents collected over a voltage range defined by the parameters of the system. These difference currents, when plotted yield a curve consisting of a peak superimposed on a baseline which is sloped (FIG. 2). The analysis routine first removes this sloped baseline and then calculates the area under the peak portion of the curve. This area is the measured signal of analyte in the sample.

The analysis routine works by noting that there is a minimum on either side of the peak. Drawing a line through the two minimum points and then subtracting the line from the curve removes the baseline offset.

The two minimum points are chosen by limiting the range that the software searches. A low range is defined on the left side of the curve (at more negative voltages) and a high range on the range on the right (at more positive voltages). Within these two ranges, two minimum points are found and used to calculate the baseline.

The routine was first tested using a simulation written in BASIC from data collected on samples. This showed that the routine worked best when run twice. Adjust the data first, then run the routine a second time to further improve results.

The routine for running the analysis is set up in six steps:
1. Find the low point in the two ranges, the low and high
2. Calculate the slope of the line drawn between these two points
3. Subtract this baselines value from the data
4. Repeat 1 through 3 above to improve accuracy
5. Calculate the area between the two minimum points
6. Convert the area to a lead concentration value and display The routine uses a series of subroutines to organize the above process and allow testing of each step. The routine "CALC_MIN" finds current value between two points and is used to find the minimum for both the high and low range.

Next the routines in "BASELINE" calculate the slope and the equation for the baseline using the two minimum points. The software then subtracts the baseline value from the difference current. Then the "CALC_MIN" and BASELIN" routines are repeated to improve the accuracy of the signal measurement. Finally, the last routine "MEASAREA" calculates the area under the curve between the two minimum points and returns a numerical result in arbitrary (A/D) units.

This value is then scaled into units of "peak area" so it can be compared with a simulation program used to test the code. For example, in blood lead measurements, routine "LOOKUP" will take the signal value and convert it to a lead concentration result, i.e., a BLL in μg/dL.

BASELINES.SRC

This routine removes the baseline offset from the original difference current curve. The procedure is to calculate the equation for the best line fitting the curve at two points and then subtract this line from the original data. The baseline equation is calculated by knowing the two minimum points, e.g., X2, Y2 which is the minimum point in the high range and X1, Y1 (the minimum point in the low range). Given these two points, the equation for the line is:

$$\text{Slope} = \frac{Y2 - Y1}{X2 - X1} \qquad 1$$

1) Calculate Y2−Y1, these are the difference current values. To increase the overall accuracy, this value is scaled by 16.
2) Calculate the X2−X1 term, these are address values. The result is a number of data points and is always positive.
3) Divide the above two numbers. This result is called the delta value and is scaled by 16 to match the scaling of the difference current values.

4) Next subtract the baseline from the difference current curve by starting with the left minimum point. Subtract the minimum point value and then the delta value multiplied by the position number. Continue this process until all the values of the curve going to the right are calculated.

5) In order to make the data look better when graphed, subtract the baseline from the curve starting from the left minimum through zero.

LOOKUP.SRC

The LOOKUP module converts the area under the curve into a final analyte value which is displayed. The routine uses a "lookup table" (see below) to perform the conversion, demonstrated here for blood lead levels (BLL) in determining lead. The table is organized into ten paired columns (EEPROM address paired with value). The table is stored in the EEPROM memory by the program. The particular system described supports eighty eight (80) sets of calibration data. The numbers are 16 bit words (2 bytes).

Column 1 of the lookup table (locations 000–0089) contains an active (working) calibration curve. It is a set of 90 calibration values of the SWC signal, corresponding to the BLL values in Column 2. This calibration curve is one of the 80 calibration curves stored in Columns 3–10, and is used by the Monitor software to calculate the BLL from a measured signal. The content of this column is updated through an electronic calibration process when a LeadCare Sensor calibration strip is used.

Column 2 (locations 0100–0189) contains a set of 90 BLL values covering the 8.5 to 62.5 $\mu$g/dL range in 0.6 $\mu$g/dL increments.

Column 3 through 10 (locations 0200–0299, 0300–0399, 0400–0499, 0500–0599, 0600–0699, 0700–0799, 0800–0899, and 0900–0999) store eight sets, each containing 100 values of the SWC signal, representing eight different calibration patterns of the signal vs. BLL dependence. Together with the BLL values in Column 1, the first 90 values of each set represent a single calibration curve. The last ten values in each table represent 10 different offsets for the upward adjustment of the stored calibration set.

Because of the limited number of entries in the table, the firmware interpolates between two values to improve the resolution of the conversion.

The lookup table (Table 1) contains information equivalent to 80 distinctively different calibration curves. During the sensor calibration step, one of these curves is selected for the measurement via a calibration strip supplied with each package of LeadCare Sensors. The selected calibration curves are loaded into Column 1 (for example, AREA= AREA1+offset1) and then become working calibration curves in the measurement of BLL.

TABLE 1

LOOKUP TABLES

| EEPROM address | Value | EEPROM address | Value | EEPROM address | Value | EEPROM address | Value | EEPROM address | Value |
|---|---|---|---|---|---|---|---|---|---|
| 0000 | AREA | 0100 | LEAD | 0200 | AREA1 | 0300 | AREA2 | 0400 | AREA3 |
| 0001 | AREA | 0101 | LEAD | 0201 | AREA1 | 0301 | AREA2 | 0401 | AREA3 |
| 0002 | AREA | 0102 | LEAD | 0202 | AREA1 | 0302 | AREA2 | 0402 | AREA3 |
| 0003 | AREA | 0103 | LEAD | 0203 | AREA1 | 0303 | AREA2 | 0403 | AREA3 |
| 0004 | AREA | 0104 | LEAD | 0204 | AREA1 | 0304 | AREA2 | 0404 | AREA3 |
| 0005 | AREA | 0105 | LEAD | 0205 | AREA1 | 0305 | AREA2 | 0405 | AREA3 |
| . | . | . | . | . | . | . | . | . | . |
| . | . | . | . | . | . | . | . | . | . |
| . | . | . | . | . | . | . | . | . | . |
| 0089 | AREA | 0189 | LEAD | 0289 | AREA1 | 0389 | AREA2 | 0489 | AREA3 |
|  |  |  |  | 0290 | OFFSET1 | 0390 | OFFSET2 | 0490 | OFFSET3 |
|  |  |  |  | 0291 | OFFSET1 | 0391 | OFFSET2 | 0491 | OFFSET3 |
|  |  |  |  | 0292 | OFFSET1 | 0392 | OFFSET2 | 0492 | OFFSET3 |
|  |  |  |  | 0293 | OFFSET1 | 0393 | OFFSET2 | 0493 | OFFSET3 |
|  |  |  |  | . | . | . | . | . | . |
|  |  |  |  | . | . | . | . | . | . |
|  |  |  |  | . | . | . | . | . | . |
|  |  |  |  | 0299 | OFFSET1 | 0399 | OFFSET2 | 0499 | OFFSET3 |
| 0500 | AREA4 | 0600 | AREA5 | 0700 | AREA6 | 0800 | AREA7 | 0900 | AREA8 |
| 0501 | AREA4 | 0601 | AREA5 | 0701 | AREA6 | 0801 | AREA7 | 0901 | AREA8 |
| 0502 | AREA4 | 0602 | AREA5 | 0702 | AREA6 | 0802 | AREA7 | 0902 | AREA8 |
| 0503 | AREA4 | 0603 | AREA5 | 0703 | AREA6 | 0803 | AREA7 | 0903 | AREA8 |
| 0504 | AREA4 | 0604 | AREA5 | 0704 | AREA6 | 0804 | AREA7 | 0904 | AREA8 |
| 0505 | AREA4 | 0605 | AREA5 | 0705 | AREA6 | 0805 | AREA7 | 0905 | AREA8 |
| . | . | . | . | . | . | . | . | . | . |
| . | . | . | . | . | . | . | . | . | . |
| . | . | . | . | . | . | . | . | . | . |
| 0589 | AREA4 | 0689 | AREA5 | 0789 | AREA6 | 0889 | AREA7 | 0989 | AREA8 |
| 0590 | OFFSET4 | 0690 | OFFSET5 | 0790 | OFFSET6 | 0890 | OFFSET7 | 0990 | OFFSET8 |
| 0591 | OFFSET4 | 0691 | OFFSET5 | 0791 | OFFSET6 | 0891 | OFFSET7 | 0991 | OFFSET8 |
| 0592 | OFFSET4 | 0692 | OFFSET5 | 0792 | OFFSET6 | 0892 | OFFSET7 | 0992 | OFFSET8 |
| 0593 | OFFSET4 | 0693 | OFFSET5 | 0793 | OFFSET6 | 0893 | OFFSET7 | 0993 | OFFSET8 |
| . | . | . | . | . | . | . | . | . | . |
| . | . | . | . | . | . | . | . | . | . |
| . | . | . | . | . | . | . | . | . | . |
| 0599 | OFFSET4 | 0689 | OFFSET5 | 0789 | OFFSET6 | 0899 | OFFSET7 | 0999 | OFFSET8 |

The firmware starts by testing that the "offset" value is not smaller or larger than the minimum or maximum value in the first column (offset) of the table. If this is to be the case, then the display will show "LOW" or "HIGH" correspondingly.

Next the first column of the table is scanned starting at the beginning for a value that is larger than the "offset" value. When this is found, the previous position is saved as "N" and the corresponding value in the lead column is saved.

As an example of using the Lookup tables in a typical analysis for blood lead levels, the firmware will perform an interpolation calculation using the formula:

$$\text{Fraction} = \frac{\text{AREA} - \text{AREA}(N)}{\text{AREA}(N+1) - \text{AREA}(N)} \times (\text{LEAD}(N+1) - \text{LEAD}(N))$$

where offset ( ) are values in the offset column and LEAD ( ) are values in the LEAD column, and offset is the original input value.

The final value is the LEAD(N)+Fraction. This is the final result of the BLL measurement which is sent to the DISPLAY module for display.

STRIP.SRC

This routine contains two tests which are performed during the processing of the sensor to determine if there are any problems with the sensor connections to the electronics. The sensor has three connections: the reference electrode (REF), the counter electrode (CE) and the working electrode (WE). A third test is needed to determine if the installed sensor is a calibration strip.

The first test (STRIPTST) checks the electrical connection between the REF electrode and the CE electrode. If the electrical connections are correct and the sensor electrodes are sufficiently covered by the test sample, the voltage of the CE electrode should be the same as the REF electrode but of opposite polarity.

The firmware checks the CE and REF electrodes by measuring the voltage of each and adding them together. The result should be zero or very close to zero. The test checks to confirm this difference is less than 100 millivolts. If the value is larger, an error flag is set (the display shows CHECK STRIP).

This test is performed every second when the analog electronics is connected to the sensor by the analog switch. (See MAIN.SRC)

The second test (TEST_WE1,TEST_WE2) checks the electrical connection to the working electrode (WE). This test works by assuming that the current being measured by the WE will change when the voltage being applied to the sensor by the CE changes.

The test is performed in two stages, the first (TEST_WE1) is to measure the current before the voltage is changed saving this value. The second, (TEST_WE2), measures the current after the voltage has changed and checks that it is different from the first. If the value has not changed by more than 125 nA the assumption is made that something is wrong with the connection to the WE and the system signals an error (the display shows CHECK STRIP).

The firmware actually checks to see if the voltage has changed by more than 50 millivolts due to limitations of the hardware. This should be noted in case the voltages from one stage to the next do not change by more than this value.

This test is conducted twice, fit when the voltage applied to the sensor is changed during transition from PRECONDITION #1 to PRECONDITION #2 stage, and second during transition from PRECONDITION #2 to DEPOSITION stage. This test is not run when the analog switch is off. It is also skipped if the time value for the stage is zero.

The third test checks whether the sensor or a calibration strip is connected to the device. The test is based on the current changing after the Precondition #1 voltage is applied to a test sensor with sample. On the other hand when a calibration strip is connected the current does not change in time.

The routine first measures the current one millisecond into the Precondition #1 and then every five milliseconds until two consecutive changes of more than 125 nA are detected. When such changes are detected the routine assumes it is a test sensor. If the current does not change within 2 seconds of the Precondition #1, a flag is set indicating that the installed sensor is actually a calibration strip.

CALSTRIP.SRC

This routine determines the size of the two resistors on the calibration strip. This is done by connecting each resistor to the output of the D/A converter, one at a time, and sequencing the voltage up in steps of 10 mV until the output is 10 mA. This technique allows using resistors in linear steps of 10 Kohms.

These two values are used to select one of the eight calibration tables stored in the EEPROM. The second value is used to select one of the ten offset values in that table. The offset value is added to all the values in the table to allow shifting that data to best match the characteristics of the LeadCare Sensor.

This is done by reading one value from the selected table, adding the selected offset, and storing the resulting value in the first table of the EEPROM.

The calibration strip code is displayed on the LCD when this process is completed. The two character code consists of a numeral (1, 2, 3, 4, 5, 6, 7, or 8) representing the table number and a letter (A, B, C, D, E, F, G, H, I, or J) representing the offset (A=1, B=2, etc.). When the calibration strip is removed, the system goes back to the "READY" mode.

As part of the sensor manufacturing process, each production batch of sensors is calibrated. One of the 80 calibration curves which are stored on the device, is selected that best matches the calibration data obtained for the current batch of sensors. This makes it possible to assign a corresponding calibration strip which will be supplied with each package of sensors produced in that batch

CALBUTN.SRC
BUTNCMDS.SRS

These two modules support the touch memory system that is used to enter calibration data into the monitor. The first module contains the two main routines, the first detects if the touch memory is connected to the connector and the second reads the data and transfers it to the EEPROM.

The touch memory input system works by having the user touch the memory button to the connector mounted on the outside of the housing. The fist routine is called every 10 milseconds by the main polling routine to detect if the memory is connected. When It is detected, the second routine is called which reads the data from the memory unit and stores it in the RAM memory. The CRC value is checked and if correct, the data is copied from the RAM to the EEPROM memory unit, If the data are not corrected, they are read again and the test is repeated. The system tries three times and then displays an error message on the display and exits.

The additional module is used to support reading and writing the memory unit using the MONITOR program. These routines allow the MONITOR program to write the calibration data values into the touch memory unit.

UPDATE.SRC

This routine outputs data to the LCD display driver. The digital data are first converted into segment data. The message symbols are obtained from flags in two variables, The data are shifted into the LCD driver using The SPI port and latched into the output registers by toggling the chip select line.

DISPLAY.SRC

This module supports the LCD unit display which is a single line, 16-character LCD; The actual drivers for the display are in the module LCD.SRC. The data displayed is based on the mode number in variable "LCDMODE."

DISPLAY MODE
1. Displays rung information and time to complete process: "TEST XXX secs" where XXX is the seconds remaining in the test
2. Displays result: "XX.X" or "HIGH" or "LOW" in selected units
3. Displays "CALIBRATION##" where ## is the code of calibration strip Routine "CLR_LCD" clears the LCD unit except for the battery message symbol.

ATOD.SRC

This module supports a 12-bit analog to digital converter such as the LTC1296 (LINEAR TECHNOLOGY, Inc.). This A/D has 8 analog inputs and interfaces to the microprocessor using the SPI, serial peripheral interface. The A/D is used to measure the current from the test sensor, the battery voltage and additional internal voltages for testing.

The firmware to support the A/D consists of two routines, one to read values and one to power down the unit for power conservation.

The first routine (AD_READ) reads one input channel of the A/D and returns the results in "ATODH, ATODL." This result is left justified in the 16 bit word. It is in 2's complement notation. The voltage reference is 4,096 volts so the scale is 1 bit=2=millivolts. The value is left justified in the 16 bit word.

The lookup table may be used following the routine to generate the address for the input multiplexor.

The second routine (ADPWROFF) sends a command to the A/D converts that puts it into a power down mode. In this mode the unit draws very little current. When a conversion is requested, the unit powers backup.

DTOA.SRC

The DTOA module supports the MAXIM 12-bit digital to analog converter. The microprocessor interfaces to the D/A using the SPI or serial peripheral interface. This D/A has a built in 2.048 volt reference. An input value of zero gives the lowest value of −2.048 volts. The highest 12-bit value of 4095 gives an output of +2.047 volts. The formula for the output voltage is:

$$\text{Output Volt} = (-2.048) + N*(1 \text{ millivolt})$$

where N is a number between 0 and 4095.

The firmware module outputs the value in variable "DA_H,DA_L" to the D/A converter using the SPI port.

RAM.SRC

This module supports the external memory which stores the collected data before it is analyzed. The hardware implementation of the RAM consists of an 8K static RAM chip and two 8-bit latches. The latches are loaded with the address of the data to be written or read. An 8-bit data bus, port C of the microprocessor, is used to load the two address latches. The lower 8-bits of the address are output on the data bus and a control line latches this data into the lower address. Similarly, the upper 8-bits of data are output on the data bus and a second control line latches these data into the upper address.

This same data bus is also connected to the input/output port of the RAM. Once the addresses are setup, another control line called READ/WRITE is used to set the RAM mode. The CHIP SELECT control line causes tie data to be read from the memory chip or written into the memory chip.

For reading data from the memory chip, the data bus is changed into an input port by setting the direction registers to zeros. When the port is an output port, the direction registers are set to one. Also because the hardware address latches are not readable, a software variable "RAMADRH, L" is used as the address data location. When a memory operation is performed, these variables are used as the address information. All memory operations are word or 2 byte operations.

The two firmware routines support reading the memory (RAM_RD) and writing data to the memory (RAM_WR). Both routines first write the address to the latches and read or write 2 bytes of data. Note that when completed, the address has been advanced to the next word.

An additional routine allows advancing the memory address (ADV_ADR) by one word.

SERIAL.SRC

This module contains support routines for the serial communications to a host computer. The serial hardware interface is setup to interrupt on incoming characters from the host computer. The routine "SERIALIRQ.SRC" handles the interrupt and sets a flag indicating a character is ready. The main routine polls this flag and if found set, goes to the communication routines in "COMMANDS.SRC." In addition, if one of the commands needs additional information, it calls routines in this module to get them.

The first routine (IN_CHAR) gets one character from the host computer. It is typically called by one of the command routines when requesting data from the host computer. It polls the character ready flag and, when set, exits back to the calling routine with the carry flag cleared. It also has a time-out timer set to 1 second. If no character is received in this time, it sounds a tone, sets the carry flag to indicate error, and exits.

The next routine (IN_NUM) is used to input a number from the host computer. The routine receives a character and tests if it is the end character (RETURN) and if so exits with the number in "TEMPH,M,L." If it is a number, It is added to the previous number by first multiplying the original number by 10 and then adding the new number. In this way, any size number can be received.

Two routines are available to output characters or numbers to the host computer. The firmware routine to output a character first tests if the RS-232 interface chip is powered on. It is normally powered off to save power. If not powered on, It is turned on and a delay of 150 milliseconds allows the power to stabilize. The character is then output to the host computer.

The second output routine is used to output a 2 byte value to the host computer as a decimal number. First the value is converted to a decimal number, then converted to ASCII code and sent to the host computer.

The last two routines send to the host computer either a single carriage return (CR) or a combination of carriage return and line-feed (CR_LF).

SERALIRQ.SRC

This module supports the interrupt from the serial interface to the host computer. The serial interface internal to the microprocessor is set to interrupt upon receiving a character from the host computer. When this occurs, this routine is called. The firmware receives the character from the serial port and tests for any errors. At this time, any hardware errors are ignored and the software exits.

The character is tested to see if it's a "CONTROL C. If so, then the command mode flag is reset, the analog switch is tuned off and the carry flag is set to indicate error. The purpose is to allow the external host computer to halt any command presently in progress and cease any activity to the sensor in case the hardware should fail and lock up in the command mode.

Next the character is tested for the START command, an "ESC" character. If it is, the command flag is set so that the next time the main routine tests for a command received, it will go to the command software routine.

Finally the character is stored in the receive variable and the data ready flag is set.

COMMANDS.SRC

The system was designed to interface to a host computer in order to allow the input of new parameters for the process. In addition to these commands, additional commands were implemented to allow testing the system during the development process.

A command packet from the host computer consists of an "ESC" character followed by a single character which defines the command. Some commands need an additional number. This is entered as a decimal number ending with a carriage return.

Below is a summary of the commands. A command can be halted by sending a "Control C" character.

SYSTEM:

| | |
|---|---|
| "R" | Resets the system by jumping to the initilization routine |

EEPROM:

| | |
|---|---|
| "A" "N" | Loads the EEPROM address, from 0 to 1023 |
| "E" "N" | Writes 16-bit value into address |
| "P" | Reads 16-bit value from address |

RAM:

| | |
|---|---|
| "Z" "N" | Loads the RAM address 0–2047 |
| "W" "N" | Writes 16-bit value into address |
| "M" | Reads 16-bit value from address |

PROCESS:

| | |
|---|---|
| "G" | Starts process |

Commands for testing:

| | |
|---|---|
| "B" | Sounds alarm tone |
| "T" | Runs filter routine on data in RAM buffer |
| "H" | Runs analysis routine on data in RAM buffer |
| "L" | Returns calculations of minimum points |
| "V" "N" | Outputs value to D/A, #N = 0 to 4095 |
| "D" "N" | Returns A/D value fram channel #N = 0 to 7 |

ROUTINES.SRC

The Pwr-Down routine is used to power down the system when it is turned off by the software. It first turns off a transistor used as an on/off switch to all external hardware. Next it sets up the microprocessor input/output ports so they can be powered down also. Finally it puts the microprocessor into a "SLEEP" mode, The system will exit this mode when the external "START" switch is pressed causing an interrupt.

The BIN2BCD routine converts a 24-bit binary number stored in TEMPH,M,L into five BCD numbers store in THOUS_10, THOUS,HUNDRED, TENS, ONES. This is done by subtracting first 10,000 from the binary number until the result is negative, then subtracting 1000, 100, and finally 10.

The BCD2BIN routine converts the BCD numbers in the five variables into a binary number.

The DIVID10 routine is used to divide the final result by 10 for display purposes. It does this by first converting to a BCD value, shifting the BCD numbers by 1 position and then reconverting to a binary number.

The BEEPER routine drives the piezo transducer to create the sound referred to as the "BEEP" or tone signal.

MATH.SRC

The math calculations contain two routes that perform mathematical functions.

The MULTI10 routine multiplies the number in TEMPM, M,L" by 10. It does his using the formula:

$$10*N=2*N+8*N$$

Multiplying by 2 and 8 are simple shift operations. The software generates the two intermediate results and then adds them to get the answer.

The divide routine divides a 16 bit value in "TEMPM, TEMPL" by a 16-bit value in "DIVSORH,DIVSORL" and returns the results in "EMPM,TEMPL."

EE_CODE.SRC

These two routines support reading and writing the EEPROM unit. This protocol requires that to read the EEPROM the upper address and command mode data be sent, then a start sequence, the lower address data, and finally a stop sequence. Now the upper address is resent, followed by a start sequence. Now the upper address is resent, followed by a start sequence and the first byte of data can be read. The second byte is read next, followed by a stop sequence sent to shut down the EEPROM.

The second routine (WRITE_EE) writes data into the EEPROM. Again the EEPROM defines the protocol. First the upper address and stop sequence are sent. Then the lower address and the first byte to be written are sent, followed by the second byte to be written and a stop sequence.

BATTERY.SRC

The battery test routine measures the battery voltage. Based on preset values, it reports if the battery is OK, low or dead.

The battery voltage is divided in half by a resistor network before being connected to the A/D converter. To compensate forte high resistance of the divider network, the clock speed of the SPI port is reduced as is the clock to the A/D converter.

The firmware starts by reading the battery voltage. The voltage is actually measured twice and averaged to reduce noise in the circuits.

Next the voltage is compared to a preset minimum value that indicates that the battery is OK. If the voltage is above this amount, the error flags are cleared and the system exits.

If the battery is below this preset minimum level, then the next step is to test to determine if the battery is below the preset "dead" level. Again, if the battery is above the dead voltage level, the error flag for low battery is set and the system exits.

If the battery is below the operational voltage level, the analog circuits will not work correctly. Even though the microprocessor system is functional, the system is halted by clearing the display and shutting off.

SELFTEST.SRC

This module contains four test routines which test the hardware when the system is first turned on. An additional two tests are done in the INIT.SRC routine. These are the tests of the internal RAM and the program memory of the microprocessor.

The first test (DATA_TST) checks the data stored in the EEPROMs first 20 locations which contain the parameters for the process run on the sensor. For example, the EEPROM when loaded by the LeadCare Monitor program, stores in location 20 the checksum of locations 1 through 19 inclusive of the EEPROM. This routine adds up these locations (1–19) and compares the result with the value In location#20. If it is the same, the data is correct. If the two numbers are different, then the carry flag is set which causes the display to show "SYSTEM ERROR #1" message.

The second test checks the analog/digital converter and digital/analog converter. It does this by outputting from the D/A a voltage and then measuring this voltage with the A/D. This is not a perfect test because the reference voltage for both systems is the D/A reference so, if it is not correct, the test may still work.

The test consists of three parts, first the D/A outputs a voltage of −2.0 volts, measures this value and determines that it is within ±2.5%. This error tolerance is to compensate for small hardware offsets in the converters. The next test output is zero volts. Finally the D/A outputs +2.0 volts. If an error is detected. The display shows "SYSTEM ERROR #2."

The third test is to check the external RAM buffer memory. This is done with a simple routine that writes the address of the location into the memory starting at location 0 and going to the end. It then reads the data and compares it with the address and checks that they are the same. If an error is detected, this condition will cause the display to show "SYSTEM ERROR #3."

At this time, the system error is reported but the system will still be allowed to run. For a production unit, the system will be shut down upon detecting an error.

The fourth test checks the checksum of lookup Table #1 against the previously calculated value stored in EEPROM. IF an error is detected, the display shows "SYSTEM ERROR #4."

EXITRQ.SRC

The external interrupt is generated whenever the START switch is pressed. The reason for having the switch connected to an external interrupt is to allow the system to be restarted when it has been powered down and put into the sleep mode. If the switch is pressed when powered down, the system is restarted by jumping to the initialization routine INIT.SEC. IF the system is already powered on, the interrupt is ignored.

The START switch is also connected to an input port which is polled in the TIMERIRQ.SRC routine which monitors the switch and sets a flag if the switch is detected on.

TIMERIRQ.SRC

The timer interrupt software is entered when the internal hardware timer of the microprocessor causes an interrupt. This interrupt rate is set for every 5 milliseconds and is very accurate as it is based on a crystal timing circuit.

The timer works by having a free running 16-bit counter incremented by the oscillator of the microprocessor. Internal circuits compare the counter value with another 167-bit register. When the two values are the same, it causes an interrupt to delay a fixed time period, first read the present value of the hardware free running counter, add it to the time delay and store this value in the compare latch. When the two latches compare, the time is up.

Upon entering his routine from an interrupt, the firmware restarts the timer hardware. This is done by getting the present count value adding to it the value equal to 5 milliseconds and storing this new value in the hardware compare register.

Next the counter decrements for the scan frequency. This will cause the scan sequence to occur at the correct frequency rate. The remaining software is run every 10 milliseconds. A flag is checked to determine if this is the second interrupt and if so, the code continues, otherwise it exits.

The remaining code is run every 10 milliseconds. It first tests the condition of the START switch. This routine debounces the switch by requiring that it be stable for 10 milliseconds before a flag is set indicating that it is on.

The next routines are used to decrement the timers that are based on the 10 millisecond time. These are used in the rest of the code to delay actions or act as time out timers.

The next section of code is activated only every second and is used to update timers that are based on 1 second time intervals.

Finally the last section of code is based on 1-minute intervals and is used to decrement the time the unit is active. If this time becomes zero, then the software goes to the routine that powers off the system. Note that the power down timer is reset whenever the START switch is pressed or a character is sent from the host computer.

CALCSUM.SRC

This routine is used during the final production of the software to calculate the checksum of the program memory space. It is run using the ICE development system. When run and halted, the CHECKSUM value is in the accumulator. This value is then stored in the checksum data field in the module DATA.SRC.

When the system is first turned on, a routine is run that calculates the program space checksum, This value is compared with the value stored in the data space. If it is the same, the program space is accepted. If different, the program memory space is no longer correct and the system halts.

CHECKSUM.SRC

This routine is run when the system is first turned on or powered back on by the START switch. This routine adds up all of program memory space to generate the checksum value. This value is compared with a value stored in the data memory location. If the two values are comparable, the program space is accepted. If the values do not agree, the program space is not correct and the system halts.

The checksum in the data memory space is calculated by the CALCSUM.SRC routine.

DATA.SRC

This module contains data which is stored in the program memory space. The first location contains the checksum of the program space for testing. The remaining space is available for storing information about a product.

VECTORS.SEC

This module is linked into the program space at the very top and contains the vector addresses for the different interrupts.

The following examples illustrate particular applications of the herein disclosed electrochemical analyzer. It will be readily apparent to a skilled artisan that changes, modifications and alterations may be made to the disclosed apparatus and software combined therewith without departing from the true scope or spirit of the invention.

EXAMPLE 1

Figure 14:
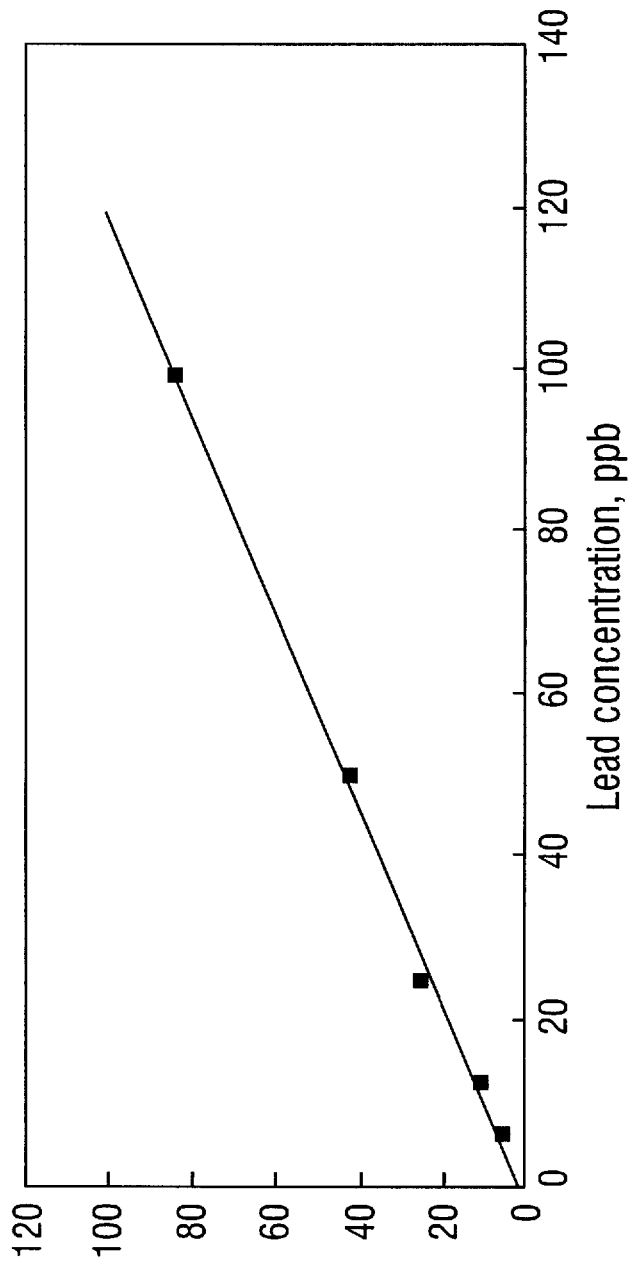
FIG. 14 is a calibration curve for lead in water using anodic stripping signals measured by the monitor with a colloidal gold sensor. Monitor parameters: 90 s deposition at −0.5V and stripping by square wave voltammetry at 100 Hz frequency, 25 mV amplitude and 2 mV steps.

The disclosed device is conveniently used to detect lead in water. FIG. 14 is a calibration curve for lead in water using anodic stripping signals measured by the monitor with a colloidal gold sensor. The electrochemical monitor parameters were: 90s deposition at −5V and stripping by square wave voltammetry at 100 Hz, 25 mV amplitude and 2 mV steps. The medium was 0.125M HCl.

Figure 17B:
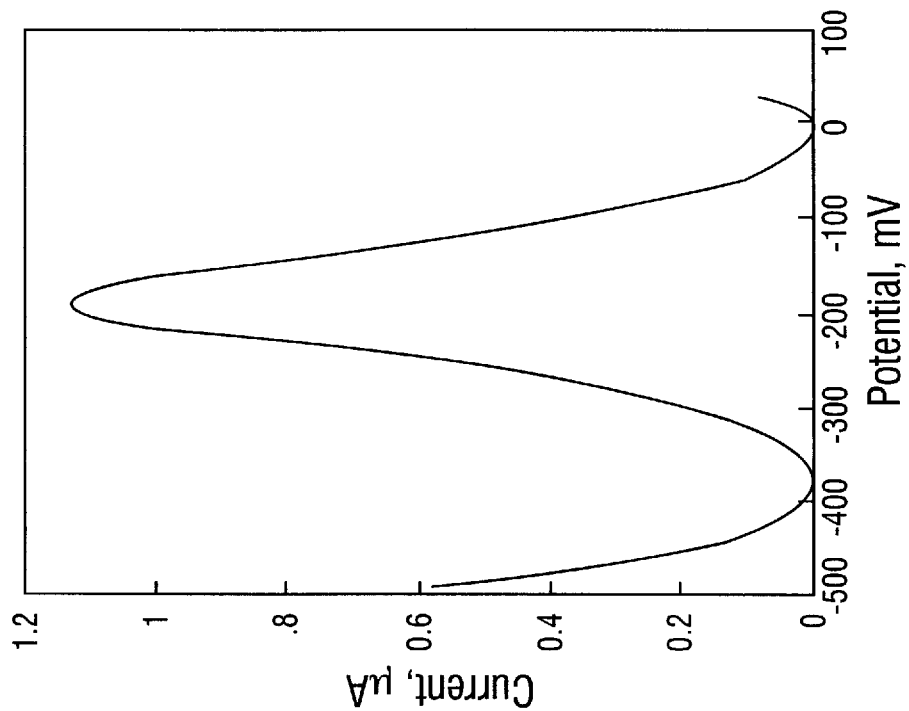
FIGS. 17A–17B compare anodic stripping curves as acquired and after processing by the invention. The curves are for a sample of 42 $\mu$g per decaliter of lead in acid treated blood using a colloidal gold electrode. Operating parameters included a 90 s deposition at −0.5V and stripping by square wave voltammetry at 80 Hz frequency, 25 mV amplitude and 2 mV steps.
Figure 17A:
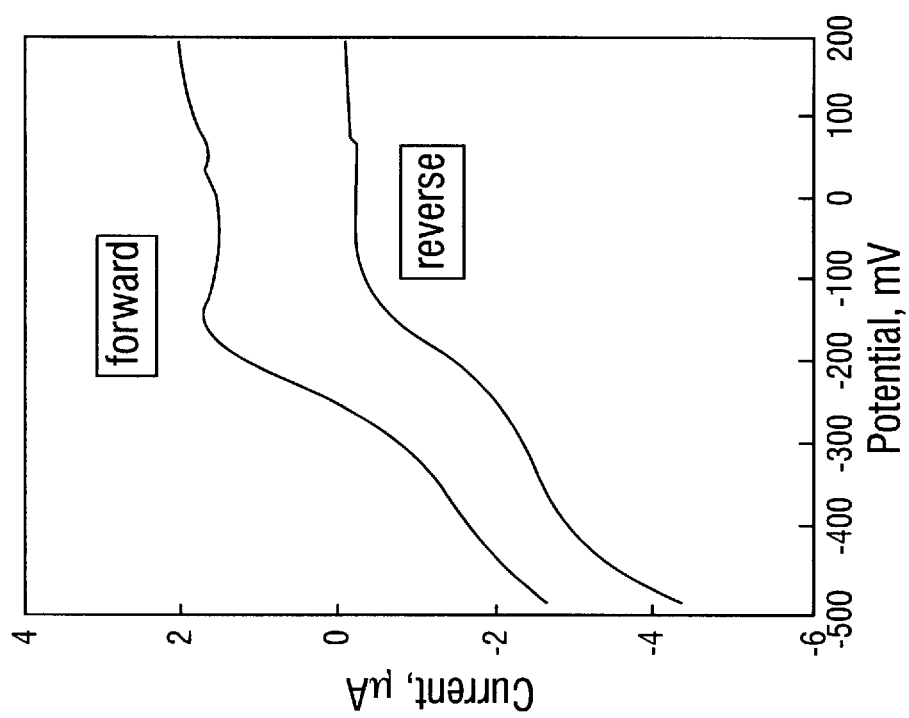

FIGS. 17A–17B compare anodic stripping curves as acquired and after processing by the invention. The curves were obtained using a 42 $\mu$g/dL lead in acid treated blood and measured using a colloidal gold sensor. Operating parameters included a 90 s deposition at −0.5V and stripping by square wave voltammetry at 80 Hz frequency, 25 mV amplitude and 2 mV steps.

The device was also used to test for lead in the presence of various metals. Results are shown in Table 2.

TABLE 2

|  |  |  |  |  | +0 ppb Pb | | +12.5 ppb Pb | | +125 ppb Pb | |
| --- | --- | --- | --- | --- | --- | --- | --- | --- | --- | --- |
| Solution tested | As, ppb | Cr(VI), ppb | Hg, ppb | Se, ppb | run #1 | run #2 | run #1 | run #2 | run #1 | run #2 |
| 1:20 dilution of TCLP Concentrate #1 | 1000 | 1000 | 50 | 1000 | 0.1 | 0.1 | 0.6 | 0.5 | 44.8 | 48.5 |
| 1:2000 dilution of TCLP Concentrate #1 | 100 | 100 | 5 | 100 |  |  | 5.1 | 8.1 | 85.2 | 86.2 |
| without TCLP Concentrate #1 added | 0 | 0 | 0 | 0 |  |  | 6.2 | 8.4 | 106.1 | 106.0 |

| Solution tested | | | | | +50 ppb Pb | |
| --- | --- | --- | --- | --- | --- | --- |
|  | Ba, ppb | Cr(VI), ppb | Ag, ppb | Cd, ppt | Pb, ppb | run #1 | run #2 |
| 1:10,000 dilution of TCLP | 50 | 50 | 50 |  |  |  |  |

Results showed that the calibration curve in the absence of tested interferences showed good linearity and reproducibility in the range of 0–100 ppb Pb. Reproducibility of the SWC signal at 12 ppb Pb level was good with a SD of 1.8 for 12 measurements with an average value of 8.7. The test solution containing As, Cr(VI),Hg and Se ions (TCLP solution) reduced the Pb signal when present at a 100-fold excess over Pb. At a 10-fold excess, there was no interference with this solution. TCLP solution #2 contained Ba, Cd, Cr(VI), and Ag and was found to increase the Pb signal at 100-fold excess over Pb.

Figure 15:
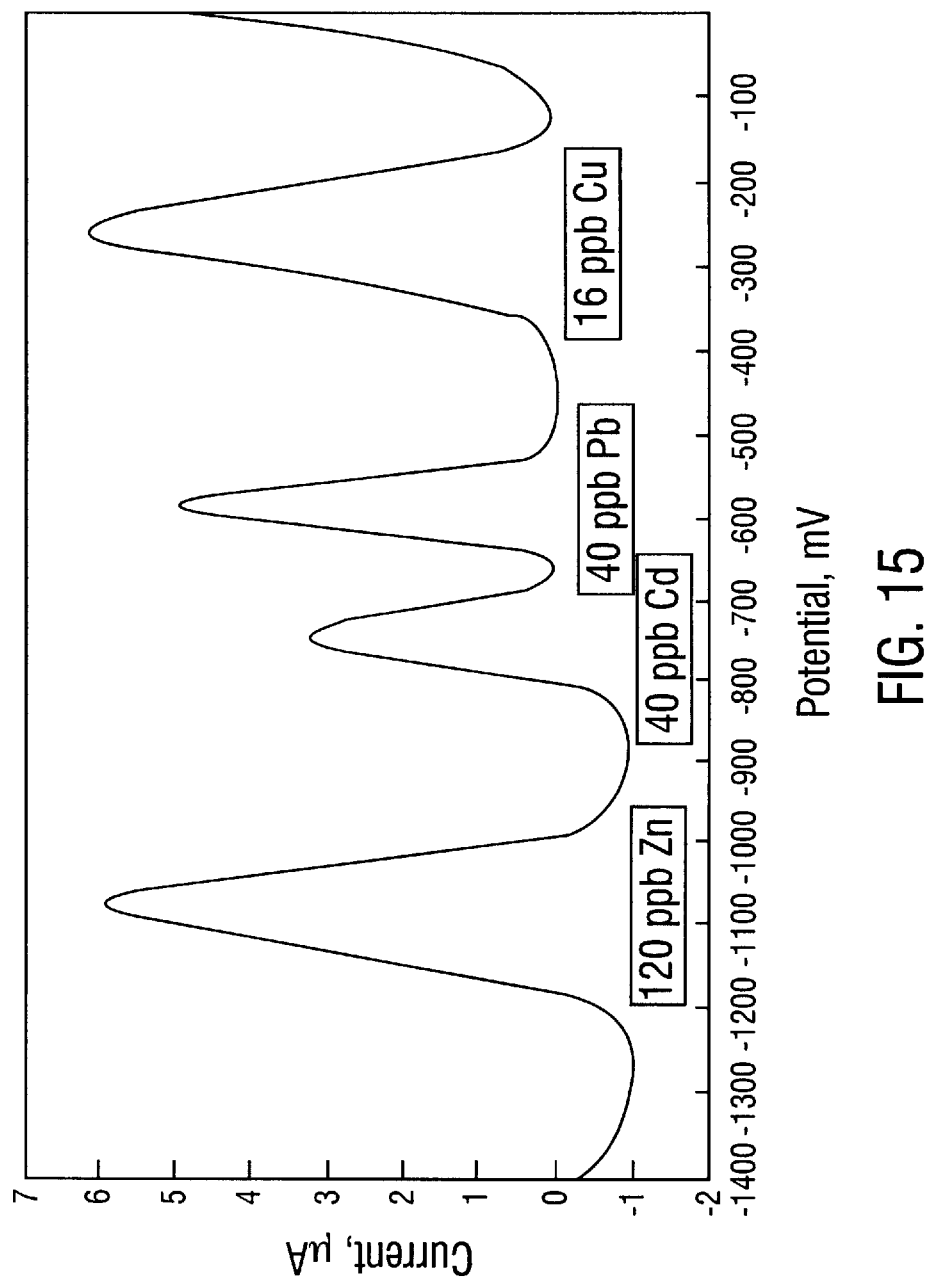
FIG. 15 shows an anodic stripping curve obtained for a mixture of four metals in 0.1M acetate buffer pH 4.2 using the monitor and a carbon sensor with in situ deposited mercury film. Monitor parameters: 240 s deposition at −1.4V and stripping by square wave voltammetry at 115 Hz frequency, 25 mV amplitude and 3 mV steps

As illustrated in FIG. 15, an anodic stripping curve was obtained for a mixture of Zn, Cd. Pb and Cu employing a carbon sensor with an in situ deposited mercury film. Instrument parameters were: 240 s deposition at −1.4 V and stripping by square wave voltammetry at 115 Hz frequencey, 25 mV amplitude and 3 mV steps.

EXAMPLE 2

The disclosed device was also used to determine cadmium concentrations. Using a colloidal gold sensor strip, samples containing cadmium ion were placed on the sensor and analyzed using the following instrumental parameters:

| 1) Delay Time And Voltage | 0 Sec | 0 mV |
| --- | --- | --- |
| 2) Precondition #1 Time And Voltage | 10 Sec | 500 mV |
| 3) Precondition #2 Time And Voltage | 10 Sec | 50 mv |
| 4) Set Deposition Time And Voltage | 90 Sec | 500 mv |
| 5) Set Equilibration Time | 0 Sec |  |
| 6) Set Voltage - Final |  | 200 mv |
| 7) Set Step Voltage, # Of Steps | 2 mv | 351 Steps |
| 1) Delay Time And Voltage | 0 Sec | 0 mV |
| 9) Set Gain, Freq | 0–10 μA | 80 HZ |
| G) Start Test And Retrieve Data (D) |  |  |
| R) Review Data |  |  |
| A) Analyze Data |  |  |
| S) Save Data |  |  |
| L) Load Lookup Table |  |  |

Figure 19:
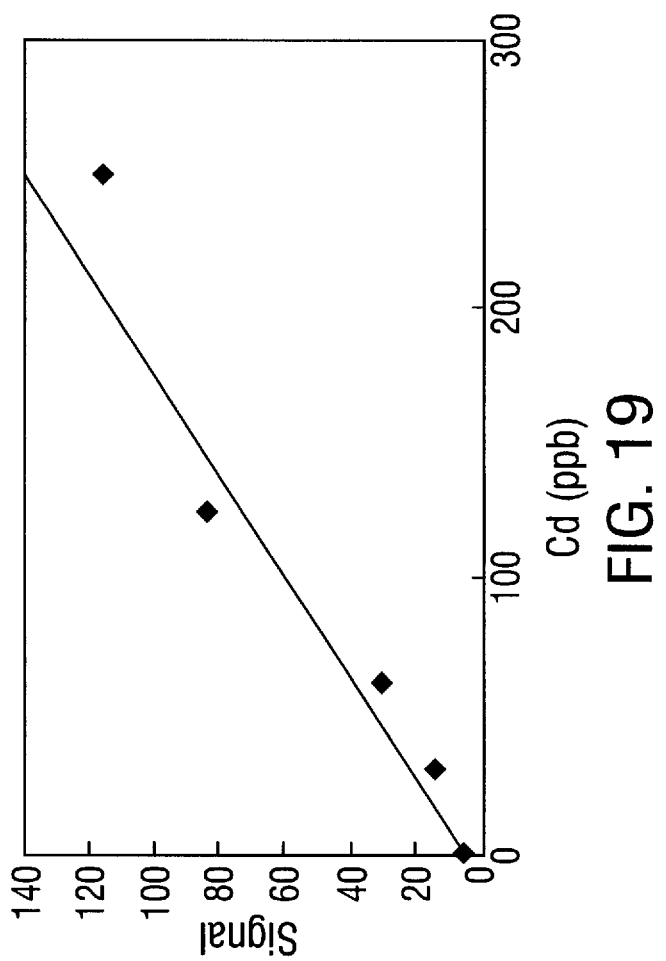
FIG. 19 shows the calibration curve for cadium ion showing the relation between the cadmium ion concentration in parts per billion and the SWC signal obtained for different amounts of cadmium in the sample.

G) Start Test And Retrieve Data (D)
R) Review Data
S) Save Data
L) Load Lookup Table
The calibration curve for cadmium ion is shown in in FIG. 19.
Table 3 shows the SWC signal for different amounts of Cd in the sample.

TABLE 3

| Cd, ppb | Signal |
| --- | --- |
| 0 | 5.3 |
| 31 | 14 |
| 62 | 31 |
| 125 | 84 |
| 250 | 116 |

Experiments involving copper(II) and cadmium(I) proved that both metals were electroactive on colloidal gold modified graphite ink electrodes and could be cathodically deposited on and anodically stripped off the gold surface. Under the solution and instrumental conditions used for measurement of lead, copper and cadmium produce stripping signals that are proportional to their respective concentrations in the ppb range. The data (not shown) indicated that copper, cadmium and lead can each be determined in the absence of the remaining two.

Simultaneous determination of more than one heavy metal in water containing several metal ions is readily accomplished with the disclosed system. One can selectively shift peak potentials of stripping peaks by complexing the metal ion, which can be accomplished by manipulation of pH and addition of specific ligands. Thus a test for simultaneous determination of the three metals from a single stripping scan is possible.

An alternative approach to determining a heavy metal in the presence of other heavy metals would be to selectively mask to allow determination of individual metals in the presence of other electroactive metals. For example, one can eliminate the anodic stripping peak of copper by adding EDTA and lowering pH of the sample to 1.0. In constrast to copper(II), lead(II) is not bound to EDTA at this pH and can be measured without interference from copper. Similar approaches using other ligands and buffering systems are expected to allow masking of other metals to determine an analyte metal in waters containing mixtures of metals.

EXAMPLE 3

Figure 13:
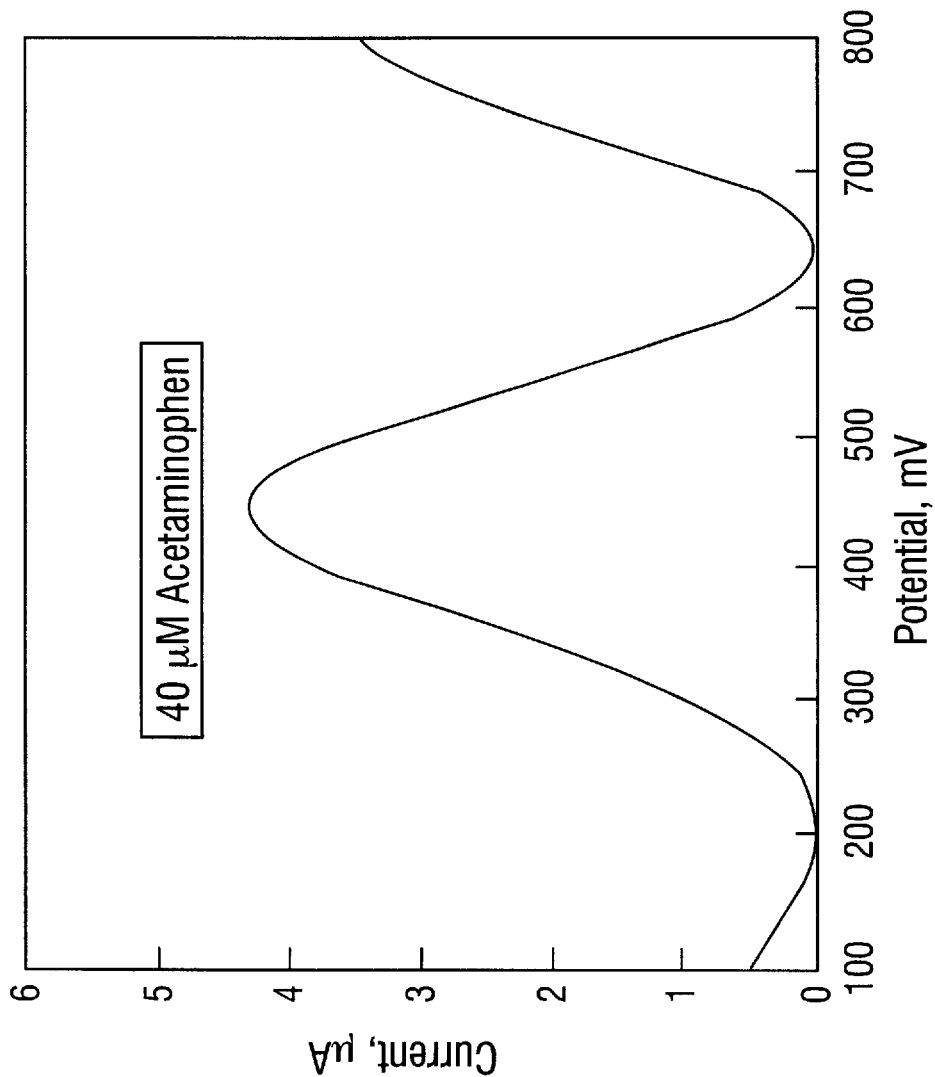
FIG. 13 is a square wave voltammetric curve of acetaminophen obtained with the disclosed device and a carbon sensor. Monitor parameters: square wave voltammetry with 100 mV initial potential, 50 Hz frequency, 25 mV amplitude and 2 mV step.

FIG. 13 shows the use of the electromonitor for the determination of a drug. The figure shows a square wave voltammetric curve of acetaminophen employing a carbon sensor. The parameters used were: square wave voltammetry with 100 mV initial potential, 50 Hz frequency, 25 mV amplitude and 2 mV steps.

Figure 16:
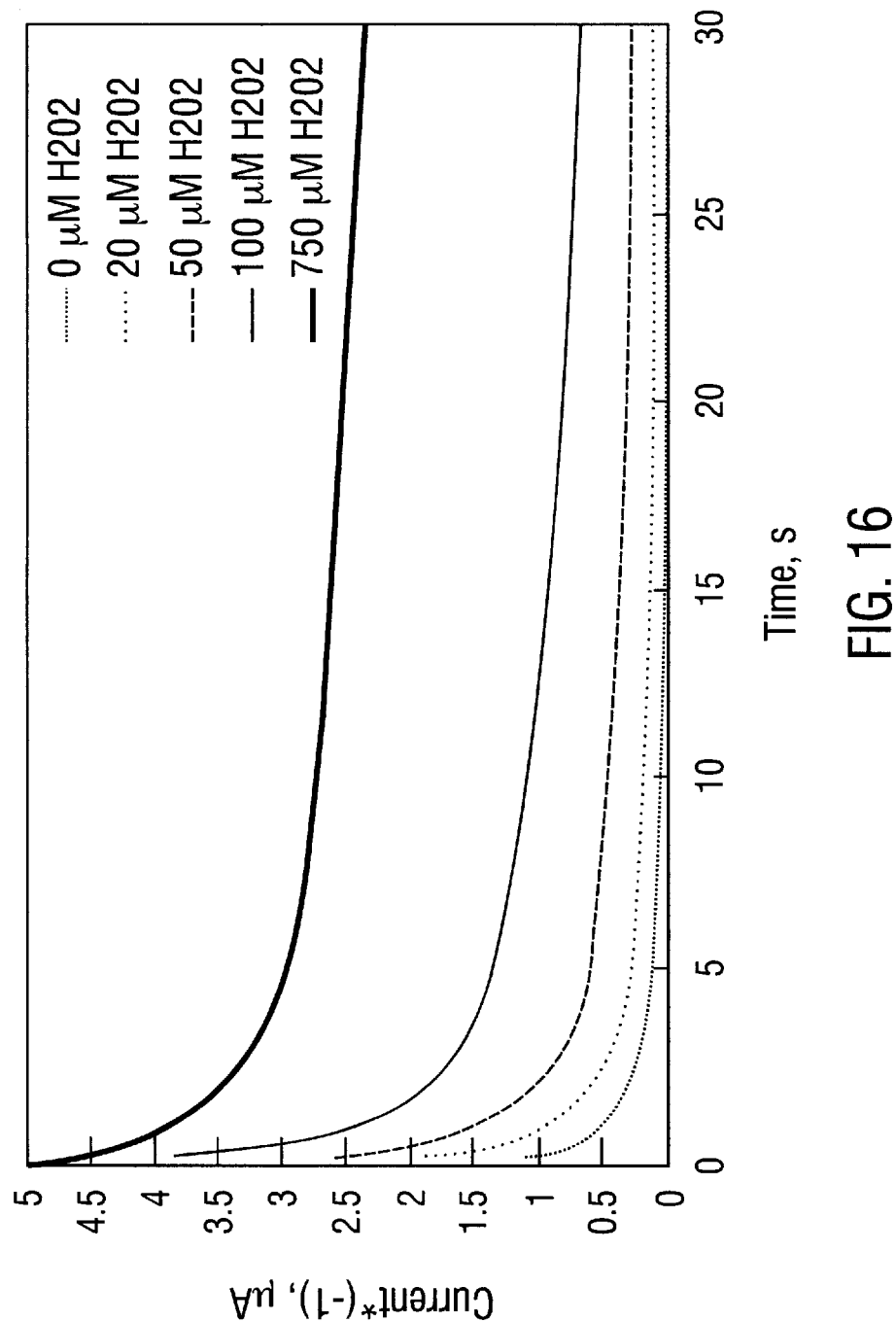
FIG. 16 shows amperometric measurement of hydrogen peroxide in 50 mM MES buffer pH 6.4 using colloidal gold-HRP (horseradish peroxidase) sensors and the disclosed device. Parameters: −100 mV potential, 4 Hz current sampling rate.

FIG. 16 illustrates the use of a collodial gold-HRP (horseradish peroxidase) sensor to measure hydrogen peroxide in 50 mM MES buffer, pH 6.4 using the disclosed device for amperometric measurement. Parameters were: −100 mV potential, 4 Hz sampling rate.

EXAMPLE 4

Figure 18:
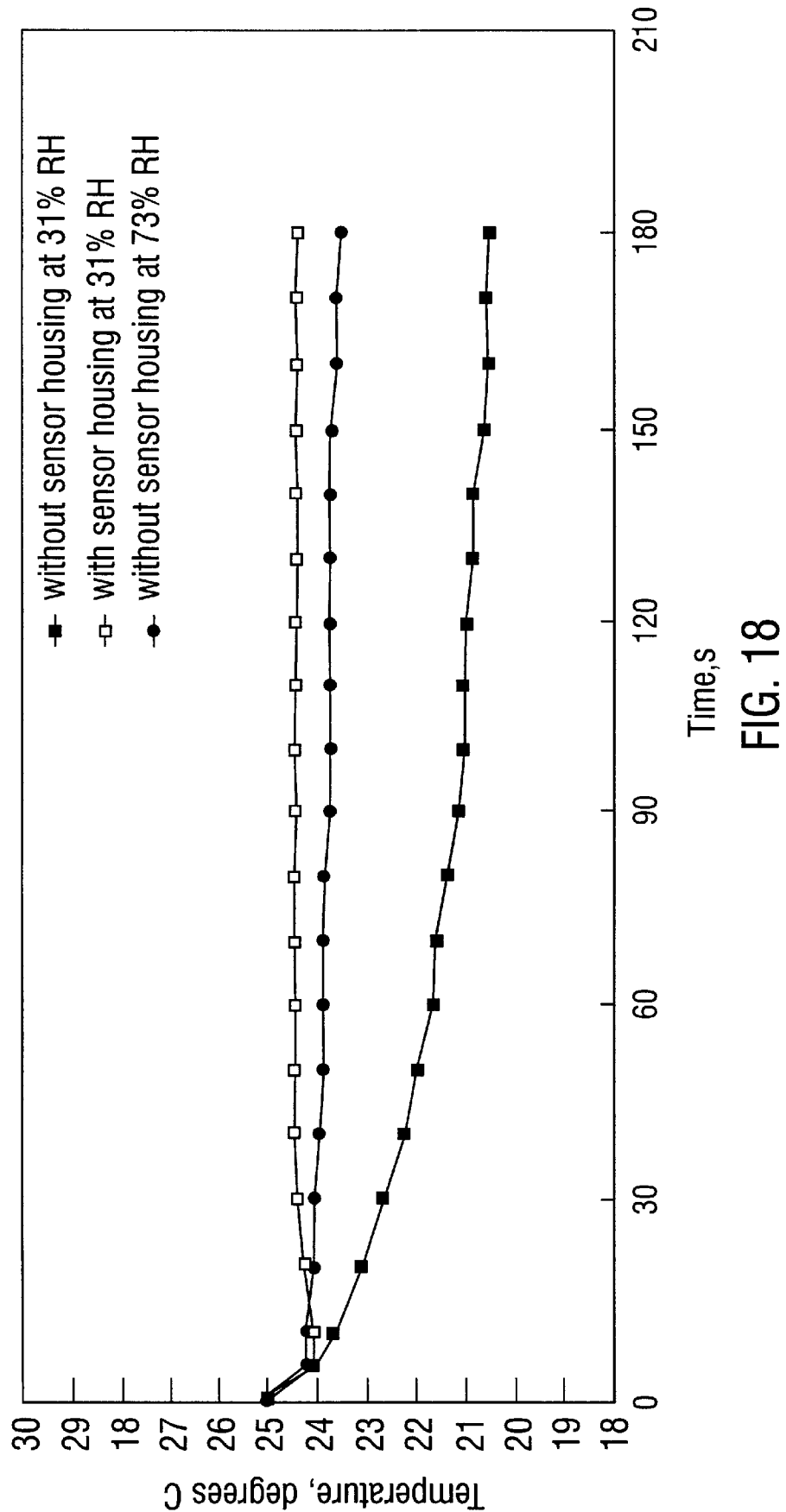
FIG. 18 shows the effect of humidity on the temperature of a sample solution placed on a colloidal gold sensor. The sample is a 50 $\mu$drop of acid treated blood.

A temperature change may severely affect current signals using sensor and arrangements that do not protect the sample solution from evaporation. As shown in FIG. 18, solution evaporation caused by low humidity produces a rapid drop in temperature on the sensor. Lower temperature results in decreased diffusion coefficient of the analyte to the sensor's working electrode which can reduce the measured signal. This effect can be reduced by using a heat sink platform enclosed in the sensor housing.

Further modifications and alternative embodiments of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as the presently preferred embodiments. Various changes may be made in the software and firmware; for example, the calibration data may be provided in multiple diskettes, partially provided from external data bases, or stored in the device itself for later analysis. Multiple ports for sensor insert may be provided and adaptations for analysis of several different analytes may be incorporated. Certain features of the invention may be utilized independently of the use of other features, all as would be apparent to one skilled in the art after having the benefit of this description of the invention.

What is claimed is:

1. Apparatus for measuring the amount of an analyte in a liquid electrolyte which comprises:

a housing substantially enclosing a data processing system including a power supply, a microprocessor, and a memory;

a sensor insertable in the housing and comprising a colloidal gold working electrode, a reference electrode and a counter electrode adapted to be in contact with a sample of said electrolyte;

an electrical connector adapted to couple signal output from the inserted sensor with the data processing system;

a microchip positioned outside the housing and containing calibration data interrelating values of said signal output with amounts of said analyte in said electrolyte;

a microchip reader on the housing operable to transfer calibration data from the microchip to the data processing system;

circuitry within the housing configured to apply a square wave coulometric analytical technique to the sensor;

a source of potential within the housing adapted to apply a potential to said circuitry; and wherein said microprocessor is programmed to apply said potential to said circuitry to measure the signal output from the sensor, and to compare said measured output signal with said calibration data to thereby determine the amount of said analyte in said electrolyte.

2. The apparatus of claim 3 wherein the microchip comprises a look up table.

3. The apparatus of claim 1 further comprising a structural module attached to said housing and configured to screen said sensor from drafts.

4. The apparatus of claim wherein the structural module includes a metal plate extending from the housing to support the sensor and serve as a heat sink for the sensor.

5. An apparatus for analyzing a metal analyte, comprising:

a colloidal gold sensor adapted at one end to be mechanically coupled to a housing and at another end contacted with a sample to be analyzed for the metal analyte, said another end including a counter-electrode; and, a microprocessor in the housing:

a) adapted to apply a sequence of potential steps to the colloidal gold electrode sufficient to cause said sensor to generate and transmit current to a data processing system through the housing;

b) adapted to communicate with a source of calibration data positioned outside the housing in a manner that will correlate current values generated and transmitted by the sensor for different amounts of said electrolyte in the sample; and c) programmed to compare currents generated and transmitted by the sensor in response to the potentials with the calibration data to thereby ascertain the amount of the analyte in the sample.

* * * * *

UNITED STATES PATENT AND TRADEMARK OFFICE
CERTIFICATE OF CORRECTION

PATENT NO. : 5,873,990

DATED : February 23, 1999

INVENTOR(S) : Marek Wojciechowski, Frederick A. Ebeling, Robert W. Henkens, Najih A. Naser, John P. O'Daly and Steven E. Wegner It is certified that error appears in the above-identified patent and that said Letters Patent is hereby corrected as shown below:

Col. 30, line 18, delete [3] and insert therefore --1--.

Col. 30, line 23, insert --3-- after "claim".

Signed and Sealed this

Twenty-ninth Day of June, 1999

Attest:

Q. TODD DICKINSON

*Attesting Officer*  *Acting Commissioner of Patents and Trademarks*

UNITED STATES PATENT AND TRADEMARK OFFICE
Certificate

Patent No.5,873,990                                                        Patented:February 23, 1999

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Marek Wojciechowski, Cary, North Carolina, Frederick A. Ebeling, Cary, North Carolina, Robert W. Henkens, Durham, North Carolina, Najih A. Naser, Durham, North Carolina, John P. O'Daly, Carrboro, North Carolina, Stven E. Wegner, Chapel Hill, North Carolina and Michael A. Harpold, Durham, North Carolina.

Signed and Sealed this Seventh Day of August, 2001.

JILL WARDEN
*Supervisory Patent Examiner*
Art Unit 1743